(12) United States Patent
Nishizawa et al.

(10) Patent No.: US 8,554,295 B2
(45) Date of Patent: Oct. 8, 2013

(54) SET FOR DETERMINING BLOOD TYPE AND COVER BODY

(75) Inventors: Yuji Nishizawa, Fujinomiya (JP); Hideto Nagata, Fujinomiya (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 468 days.

(21) Appl. No.: 12/933,107

(22) PCT Filed: Feb. 26, 2009

(86) PCT No.: PCT/JP2009/053485
§ 371 (c)(1), (2), (4) Date: Sep. 17, 2010

(87) PCT Pub. No.: WO2009/116370
PCT Pub. Date: Sep. 24, 2009

(65) Prior Publication Data
US 2011/0021890 A1    Jan. 27, 2011

(30) Foreign Application Priority Data

Mar. 21, 2008  (JP) ................................. 2008-073635

(51) Int. Cl.
*A61B 5/1455*  (2006.01)
*A61B 5/00*  (2006.01)

(52) U.S. Cl.
USPC ............ 600/310; 600/322; 600/323; 600/573

(58) Field of Classification Search
USPC ................. 600/309, 310, 322, 331, 340, 341, 600/344, 473, 476, 573, 584; 200/332.2, 200/342
See application file for complete search history.

(56) References Cited

U.S. PATENT DOCUMENTS 3,646,298 A * 2/1972 Weber et al. ............... 200/332.2
4,615,340 A  10/1986 Cronenberg et al.
(Continued)

FOREIGN PATENT DOCUMENTS

CN  1961827 A  5/2007
JP  2004-16297 A  1/2004
(Continued)

OTHER PUBLICATIONS

Chinese Office Action (Rejection of the Application) dated Jun. 28, 2012, issued in corresponding Chinese Patent Application No. 200980103789.0, and partial English language translation of Office Action. (6 pages).

(Continued)

*Primary Examiner* — Eric Winakur
*Assistant Examiner* — Chu Chuan (JJ) Liu
(74) *Attorney, Agent, or Firm* — Buchanan Ingersoll & Rooney PC

(57) ABSTRACT

Disclosed is a set for determining whether blood obtained in puncture tools by puncturing a blood vessel is venous blood or arterial blood easily, and ensuring handling under a sterile state. A set for determining blood type has a cover body to be attached to a syringe set, and a blood type determination unit to be housed in the cover body. The blood type determination unit comprises a light projecting portion and a light receiving element, and a blue output LED and a red output LED showing a judgment result based on a signal obtained from the light receiving element. The cover body has a body and a lid that are combined with each other to cover the blood type determination unit, a partition for passing blood between the light projecting portion and the light receiving element, and a pair of measurement windows for transmitting light between the light projecting portion and the light receiving element through the partition.

11 Claims, 22 Drawing Sheets

(56) References Cited

U.S. PATENT DOCUMENTS

| | | | |
|---|---|---|---|
| 4,913,150 A * | 4/1990 | Cheung et al. | 600/323 |
| 5,249,584 A | 10/1993 | Karkar et al. | |
| 5,385,539 A * | 1/1995 | Maynard | 604/6.08 |
| 7,171,251 B2 * | 1/2007 | Sarussi et al. | 600/324 |
| 2008/0177163 A1 * | 7/2008 | Wang et al. | 600/324 |
| 2010/0036218 A1 | 2/2010 | Wang et al. | |

FOREIGN PATENT DOCUMENTS

| | | |
|---|---|---|
| JP | 2006-288835 A | 10/2006 |
| JP | 2007-209 A | 1/2007 |
| WO | WO 98/37801 A1 | 9/1998 |

OTHER PUBLICATIONS

Supplementary European Search Report dated Mar. 23, 2011, issued in corresponding European Patent Application No. 09 72 2826.

International Search Report (PCT/ISA/210) issued on Mar. 31, 2009, by Japanese Patent Office as the International Searching Authority for International Application No. PCT/JP2009/053485.

Written Opinion (PCT/ISA/237) issued on Mar. 31, 2009, by Japanese Patent Office as the International Searching Authority for International Application No. PCT/JP2009/053485.

* cited by examiner

SET FOR DETERMINING BLOOD TYPE AND COVER BODY

TECHNICAL FIELD

The present invention relates to a set for determining blood type which includes a blood type determination unit for determining, by optical means, whether blood obtained is venous blood or arterial blood, and a cover body for covering the blood type determination unit, and also relates to the cover body.

BACKGROUND ART

The cases of puncturing a blood vessel with a hollow needle include a case of puncturing a vein and a case of puncturing an artery, depending on the purpose of puncturing, such as collecting blood, insertion of a catheter, etc. When a blood vessel is punctured, blood flows into a puncture tool such as a transparent syringe. A skilled person can judge whether the blood obtained is venous blood or arterial blood, based on the color of the blood obtained. However, it may be difficult for an unskilled person to make such a judgment.

Since oxygen saturation of blood is low in veins and high in arteries, whether the blood obtained is venous blood or arterial blood can be determined also by measuring the oxygen saturation of the blood obtained. Measurement of the oxygen saturation can be made, for example, by use of a measuring instrument described in Japanese Laid-Open Patent Publication No. 2006-288835. In this instrument, light emitted from a light emitting element is transmitted through blood (the measurement object) before being received by a light receiving element, and whether the blood is venous blood or arterial blood can be determined based on the band characteristic of the wavelength of the light received. By use of a device based on such a principle, even an unskilled person can easily judge whether the blood obtained is venous blood or arterial blood, which is convenient.

In medical procedures, for example, during a surgical operation, the operating surgeon and the like who make direct contact with a patient are, in principle, permitted to touch only medical instruments that have been sterilized.

However, the device described in the above-mentioned Japanese Laid-Open Patent Publication No. 2006-288835 has the light emitting element, the light receiving element, a power supply, a control unit, etc. and is therefore difficult to sterilize; accordingly, the device cannot be used as it is for a surgical operation or the like.

DISCLOSURE OF INVENTION

It is an object of the present invention to provide a set for determining blood type and a cover body, which are capable of easily determining whether blood collected by puncturing a blood vessel with a puncture tool is venous blood or arterial blood and which can be operated in a sterile condition.

A set for determining blood type according to the present invention includes a cover body to be attached to a puncture tool, and a blood type determination unit to be housed in the cover body. The blood type determination unit includes a light projecting section and a light receiving section which are located so as to face each other, a judging section for determining whether blood between the light projecting section and the light receiving section is venous blood or arterial blood, based on a signal obtained from the light receiving section, and an output section for outputting the result of judgment made by the judging section. The cover body has a measurement section to be attached to the puncture tool such that blood collected by the puncture tool flows into a space between the light projecting section and the light receiving section.

Thus, the blood type determination unit is covered with the cover body so that it will not be touched by a human hand, and projection and reception of light with respect to the puncture tool are carried out though the measurement window, whereby whether the blood obtained by the puncture tool is venous blood or arterial blood can be determined easily. The cover body is simple in structure, and can be prepared as a preliminarily sterilized disposable article, so that the blood type determination unit can be operated in a sterile condition. Here, the sterile condition includes an aseptic condition.

The cover body may have a first cover member having the measurement section and in which the blood type determination unit is mounted, and a second cover member connected to the first cover member by a hinge. In such a configuration, the blood type determination unit can be covered simply by folding the second cover member, so that simple operation is ensured.

The measurement section may have an attachment portion to be attached to the puncture tool, and a measurement window provided on the attachment portion and through which light is transmitted between the light projecting section and the light receiving section. The measurement window may not necessarily be a perfect transparent body, insofar as light (inclusive of infrared light other than visible light) can be transmitted through the measurement window to such an extent that the transmitted light is measurable.

In the measurement section, at least a periphery of the measurement window may be lightproof. Owing thereto, influence of disturbance light on the light projecting section and the light receiving section are lessened, and thus, stable determination can be performed.

The puncture tool may have a needle body and a syringe, the attachment portion may have a blood inflow portion which is disposed between the needle body and the syringe and into which blood is introduced, and the needle body and the syringe may be connected to the blood inflow portion. Such a blood inflow portion can be configured to be appropriately small in diameter and hence can be filled up with blood speedily. Accordingly, early determination of blood type can be performed. Also, this cover body is applicable to general-purpose syringes and needle bodies.

The puncture tool may have a needle body and a syringe, and the attachment portion may be attached to an outer cylinder of the syringe. A cylindrical body of the syringe is normally transparent, so that blood type can be judged through the cylindrical body.

The puncture tool may have a needle body and a syringe, and the attachment portion is attached to a blood inflow portion which is formed at a hub of the needle body and into which blood is introduced. The hub of the needle body is small in size and is accordingly filled up with blood speedily. Thus, early determination of blood type can be performed.

The output section may have a first lamp for emitting light when the result of judgment by the judging section is venous blood, and a second lamp for emitting light when the result of judgment by the judging section is arterial blood. With such first and second lamps, the judgment result can be easily recognized.

The blood type determination unit may have a power switch, and the cover body may have a switch operating section which, when the blood type determination unit is placed therein, abuts against the power switch to turn on a power supply for the blood type determination unit. By operating the power switch with the switch operating section as above, the power supply for the blood type determination unit is automatically turned on simply by inserting the blood type determination unit into the cover body, so that easy operation is ensured.

The puncture tool may have a needle body and a syringe, and the cover body may have a syringe holding member for holding the syringe. With such a syringe holding member, the cover body can be attached to the syringe easily and reliably, so that stable operation can be ensured.

A cover body according to the present invention houses therein a blood type determination unit and is attached to a puncture tool, the blood type determination unit including a light projecting section and a light receiving section that are located so as to face each other, a judging section for determining whether blood between the light projecting section and the light receiving section is venous blood or arterial blood, based on a signal obtained from the light receiving section, and an output section for outputting the result of judgment by the judging section. The cover body includes a measurement section to be attached to the puncture tool such that blood collected by the puncture tool flows into a space between the light projecting section and the light receiving section.

As described above, the blood type determination unit is covered with the cover body so that it will not be touched by a human hand, and projection and reception of light with respect to the puncture tool is carried out through the measurement section, whereby whether blood obtained by the blood collecting body is venous blood or arterial blood can be determined easily. This cover body is simple in structure and can be prepared as a preliminarily sterilized disposable article, so that the blood type determination unit can be operated in a sterilized condition.

BEST MODE FOR CARRYING OUT THE INVENTION

Now, a set for determining blood type and a cover body according to the present invention will be described below by showing first to third embodiments thereof and referring to the accompanying FIGS. 1 to 22. First, a set 10a for determining blood type and a cover body 12a according to the first embodiment will be described.

Figure 1:
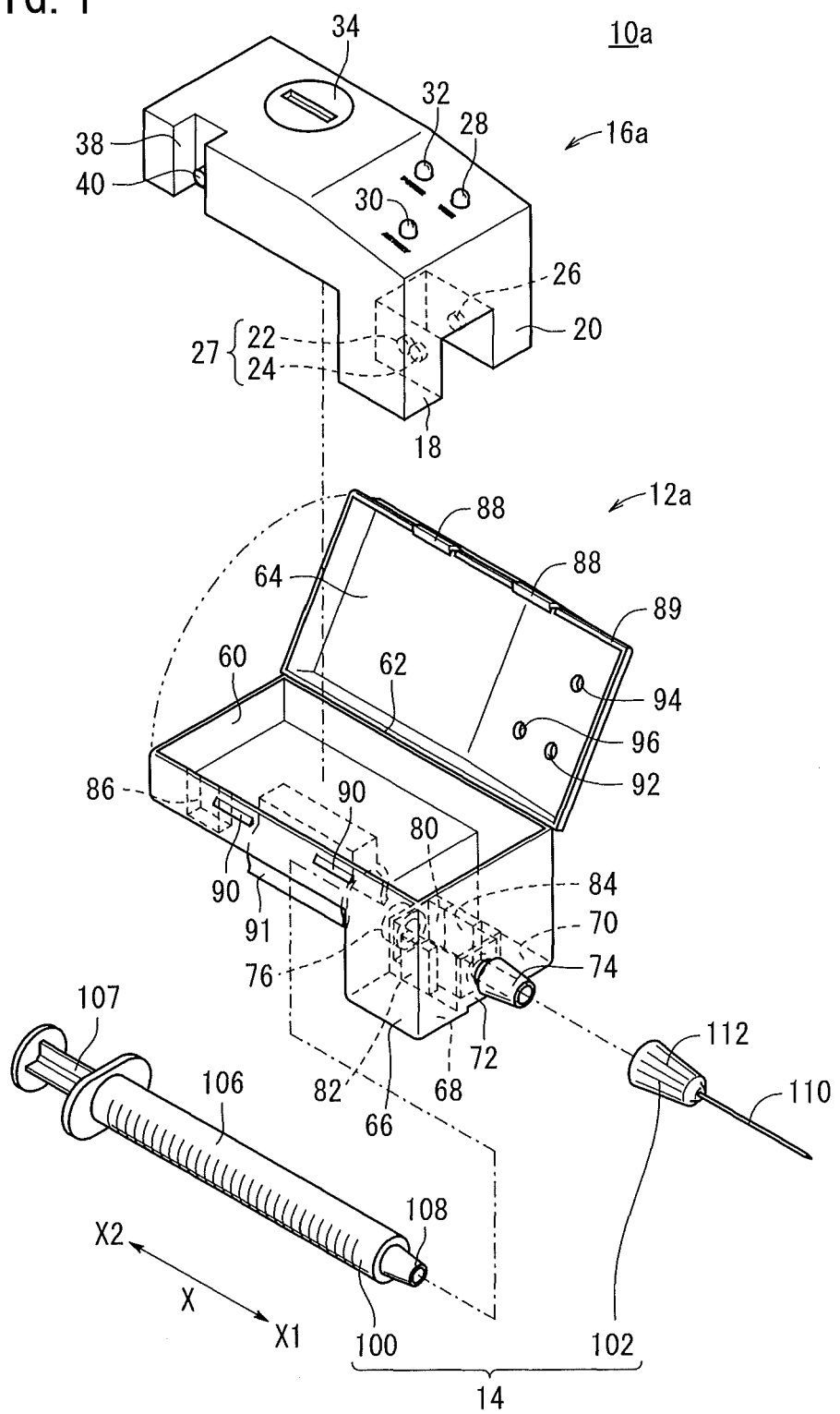
FIG. 1 is an exploded perspective view of a set for determining blood type according to a first embodiment of the present invention.
Figure 2:
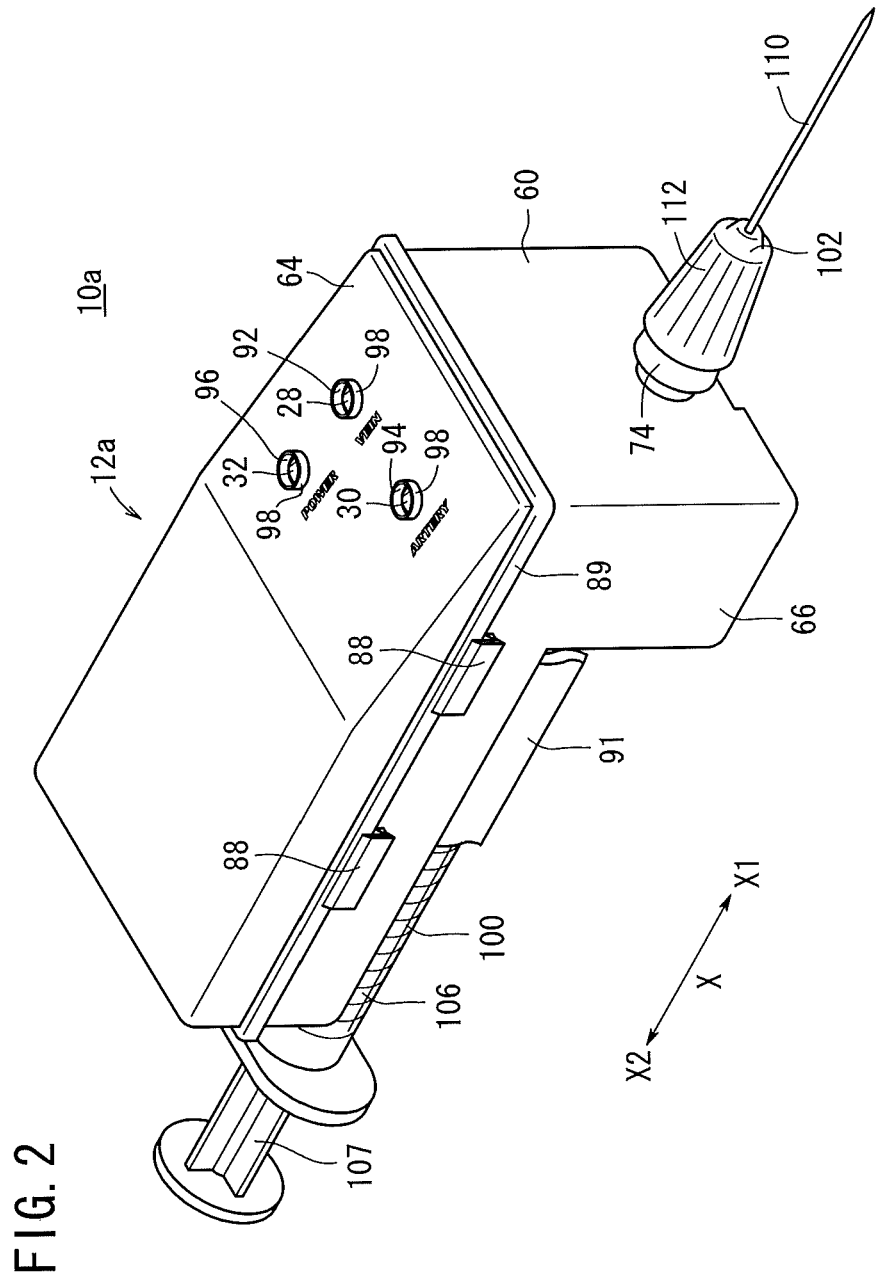
FIG. 2 is a perspective view of the set for determining blood type according to the first embodiment.
Figure 3:
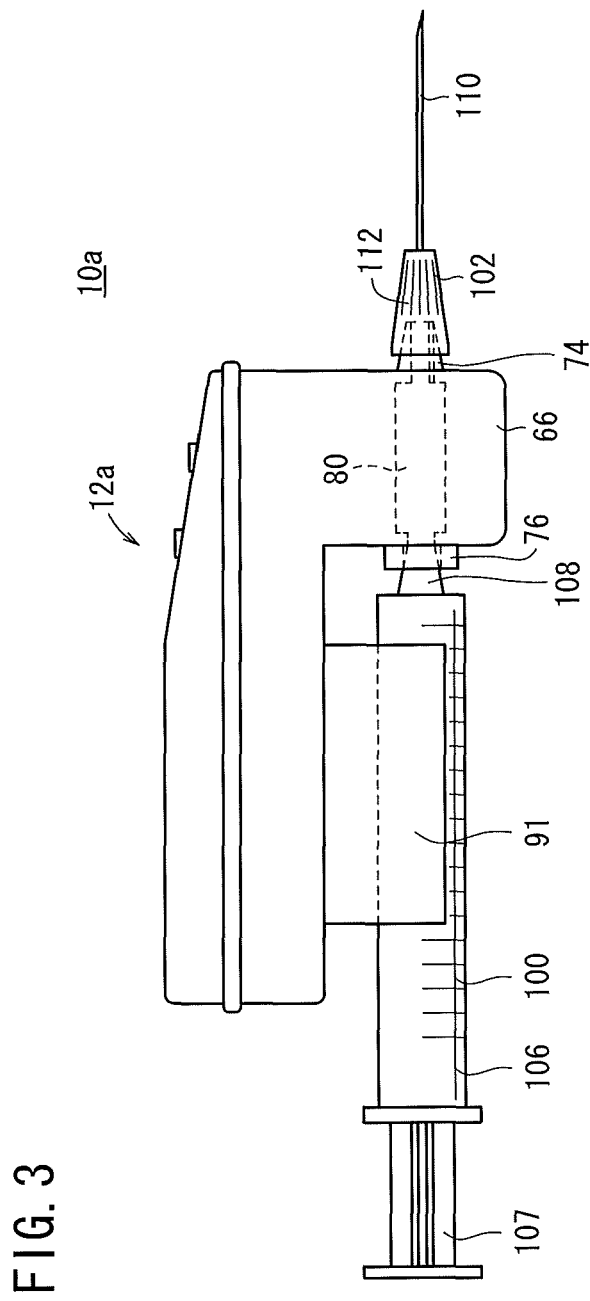
FIG. 3 is a side view of the set for determining blood type according to the first embodiment.

As shown in FIGS. 1, 2 and 3, the set 10a for determining blood type, which is to be applied to a syringe set (puncture tool) 14, has the cover body 12a to be attached to the syringe set 14, and a blood type determination unit 16a to be housed in the cover body 12a.

Figure 4:
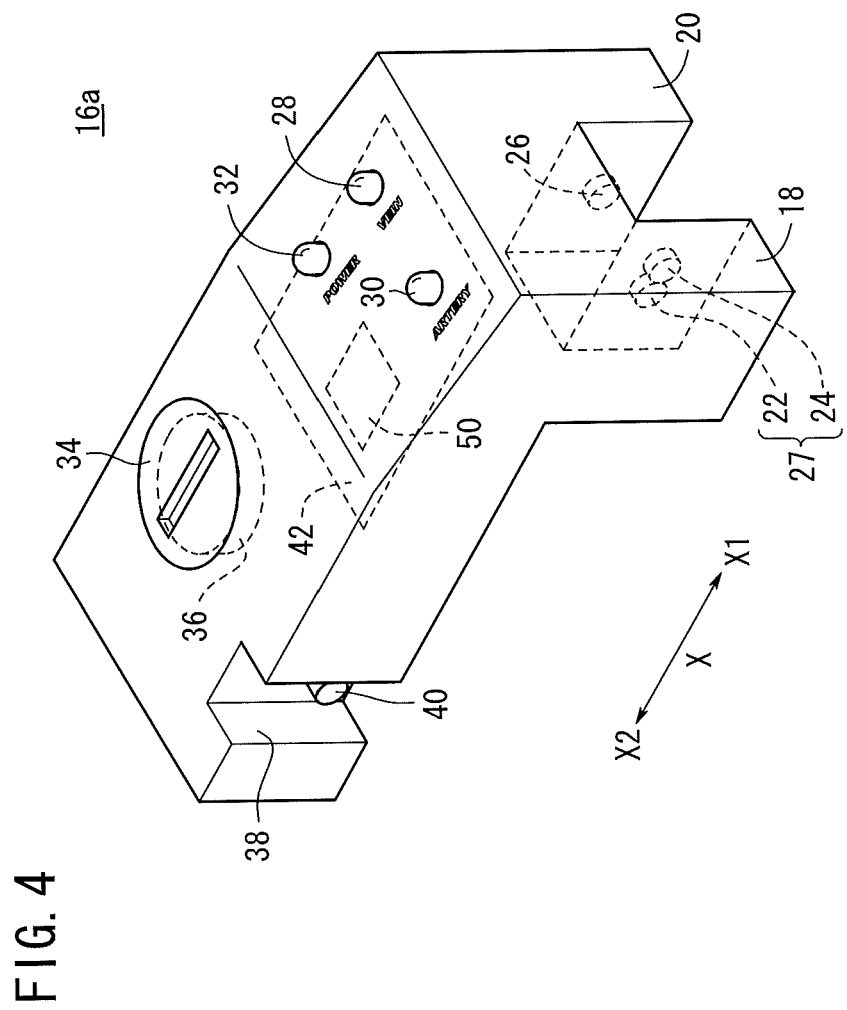
FIG. 4 is a perspective view of a blood type determination unit.

As shown in FIG. 4, the blood type determination unit 16a is substantially plate-like in shape, and has a pair of swollen portions 18 and 20 projected downward from an end portion in a distal direction (hereinafter also referred to as X1-direction, with the opposite direction also referred to as X2-direction, and with the longitudinal direction referred to as X-direction) thereof. A red measurement LED (light projecting section) 22 and an infrared measurement LED (light projecting section) 24 are provided at an inner side surface of the swollen portion 18, whereas a light receiving element (light receiving section) 26 is provided at an inner side surface of the swollen portion 20. The red measurement LED 22 and the infrared measurement LED 24 are located so as to face the light receiving element 26, so that the light receiving element 26 can receive lights emitted from the red measurement LED 22 and the infrared measurement LED 24. The red measurement LED 22 and the infrared measurement LED 24 will collectively be also referred to as a light projecting section 27.

A blue output LED (output section; first lamp) 28 for displaying detection of venous blood, a red output LED (output section; second lamp) 30 for displaying detection of arterial blood, and a green LED 32 serving as a power supply lamp are provided at a portion of an upper surface of the blood type determination unit 16a which is near an end in the X1-direction. The surrounding part of these lamps has a gently inclined surface slanted down along the X1-direction, thereby enhancing visibility of the blue output LED 28, the red output LED 30 and the green LED 32. In view of the fact that venous blood is comparatively dark in color, the blue output LED 28 is used for displaying detection of venous blood. In view of the fact that arterial blood is comparatively red in color, the red output LED 30 is used for displaying detection of arterial blood. This permits the operator to recognize the judgment result in an intuitive manner. Letters "VEIN" are presented in the vicinity of the blue output LED 28, letters "ALTERY" in the vicinity of the red output LED 30, and letters "POWER" in the vicinity of the green LED 32, whereby easy understanding of the functions of the LEDs is ensured.

A cell lid 34 is provided at a portion of the upper surface of the blood type determination unit 16*a* which is near an end in the X2-direction. The cell lid 34 can be detached by such an operation as turning with a screw driver, so that a cell 36 disposed inside can be replaced. The cell 36 is, for example, a button cell.

In a side surface of the blood type determination unit 16*a*, there is provided a groove 38 communicating with the upper surface and a lower surface of the blood type determination unit 16*a*, and a momentary-type power switch 40 is provided at a bottom portion of the groove 38. Since the power switch 40 is provided in the groove 38, it would not be pushed carelessly. The power switch 40 functions also as measurement start instructing means, and, when the power switch 40 is pushed, the blood type determination unit 16*a* begins to perform measurement after a predetermined initial processing. A control board 42 is provided inside the blood type determination unit 16*a*.

Figure 5:
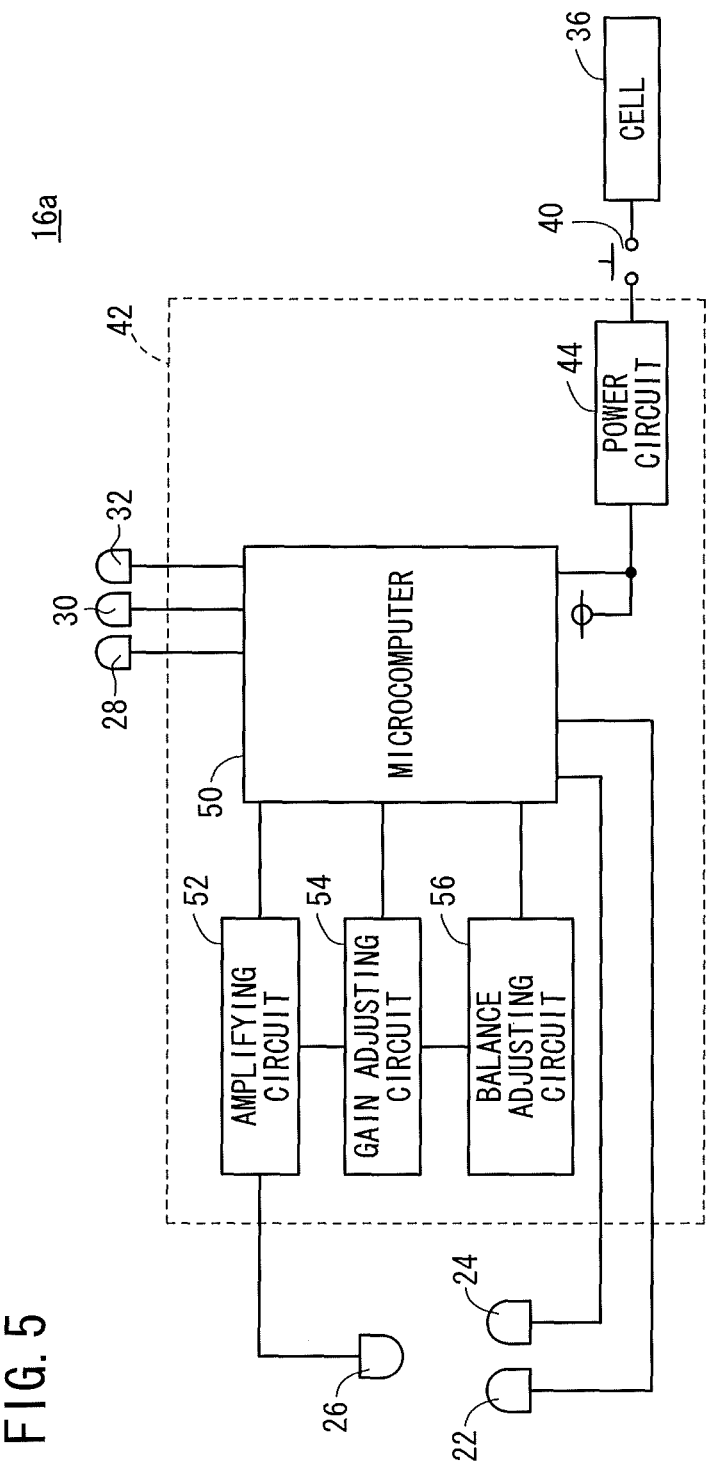
FIG. 5 is a block diagram of the blood type determination unit.

As shown in FIG. 5, the power switch 40 is provided between the cell 36 and the control board 42. With the power switch 40 pushed, a power circuit 44 on the control board 42 is supplied with electric power, and various functional sections are energized through the power circuit 44, whereby the blood type determination unit 16*a* is started.

The control board 42 has a microcomputer (judging section) 50 for generally controlling the blood type determination unit 16*a*, an amplifying circuit 52 for amplifying a signal outputted from the light receiving element 26 upon reception of light, a gain adjusting circuit 54 for adjusting the gain of the amplifying circuit 52, and a balance adjusting circuit 56 for balancing a signal. The signal amplified by the amplifying circuit 52 is supplied to the microcomputer 50. Such amplifying circuits 52 may be provided in a plurality of stages. The gain adjusting circuit 54 and the balance adjusting circuit 56 are controlled by the microcomputer 50. The red measurement LED 22, the infrared measurement LED 24, the blue output LED 28, the red output LED 30 and the green LED 32 are turned on/off under the operation of the microcomputer 50. For each of the red measurement LED 22 and the infrared measurement LED 24, a circuit for adjusting the luminance in emission may be provided.

The microcomputer 50 has an MPU, a ROM, a RAM and the like, and a program recorded in the ROM is read and executed, whereby a predetermined software-based processing is carried out.

Specifically, upon being supplied with electric power, the microcomputer 50 performs a predetermined initial checking, and turns on the green LED 32 if there is no abnormal condition. Next, the microcomputer 50 turns on the red measurement LED 22 and the infrared measurement LED 24 in a predetermined sequence, and reads through the amplifying circuit 52 the signal outputted by the light receiving element 26 upon reception of light. As will be described later, blood as a measurement object flows between the light projecting section 27 and the light receiving element 26, and, therefore, the light receiving element 26 receives the light having been transmitted through the blood.

Meanwhile, oxygenated hemoglobin, which is abundant in arterial blood, has a property of absorbing infrared light (i.e., the light emitted from the infrared measurement LED 24 and having a wavelength of, for example, 880 nm) more strongly than red light (i.e., the light emitted from the red measurement LED 22 and having a wavelength of, for example, 657 nm). On the other hand, reduced hemoglobin, which is abundant in venous blood, has a property of absorbing red light stronger than infrared light. Therefore, discrimination between venous blood and arterial blood can be performed based on the signal obtained from the light receiving element 26. The microcomputer 50 performs a determination (judgment) corresponding to such a discrimination. Upon determination of venous blood, the microcomputer 50 turns the blue output LED 28 on and turns the red output LED 30 off. Upon determination of arterial blood, the microcomputer 50 turns the red output LED 30 on and turns the blue output LED 28 off.

In a predetermined short period after the power supply is turned on, all the blue output LED 28, the red output LED 30 and the green LED 32 may be turned on so that it can be confirmed that such troubles as lowering in the voltage of the cell 36 and line breakage are absent.

When the voltage of the cell 36 has been lowered, the green LED 32 may be made to blink, thereby issuing an alarm indicative of the lowering in the voltage.

A configuration may be adopted in which the blue output LED 28 and the red output LED 30 are both kept on while a judging process for determination is being conducted after turning-on of the power supply, and, after the judge processing is finished, either one of the two LEDs is turned off based on the judgment result. In this case, the green LED 32 may be omitted.

While the judging process for determination is being conducted, the blue output LED 28 and the red output LED 30 may be made to blink, thereby indicating that the judging process is being carried out.

In addition, where it has been failed to determine whether the blood in question is venous blood or arterial blood, both the blue output LED 28 and the red output LED 30 may be turned on to indicate occurrence of a measurement error.

The blood type determination unit 16*a* configured as above is basically used in the state of being housed in the cover body 12*a*.

Returning to FIGS. 1 to 3, the cover body 12*a* has a main body (first cover member) 60 in which to mount the blood type determination unit 16*a*, and a lid (second cover member) 64 of which a longer edge portion is connected to the main body 60 by a hinge 62. The cover body 12*a* is formed from a resin material (e.g., polyolefin or the like).

The main body 60 has a box-like shape which is opened on the upper side and in which the blood type determination unit 16*a* is to be mounted. The main body 60 has a swollen portion (measurement section) 66 projecting downward from its end portion in the X1-direction, and is L-shaped in side view (see FIG. 3).

The swollen portion 66 has recesses 68 and 70 in which the above-mentioned swollen portions 18 and 20 are to be inserted, and a partition (attachment portion) 72 provided between the recesses 68 and 70.

Figure 6:
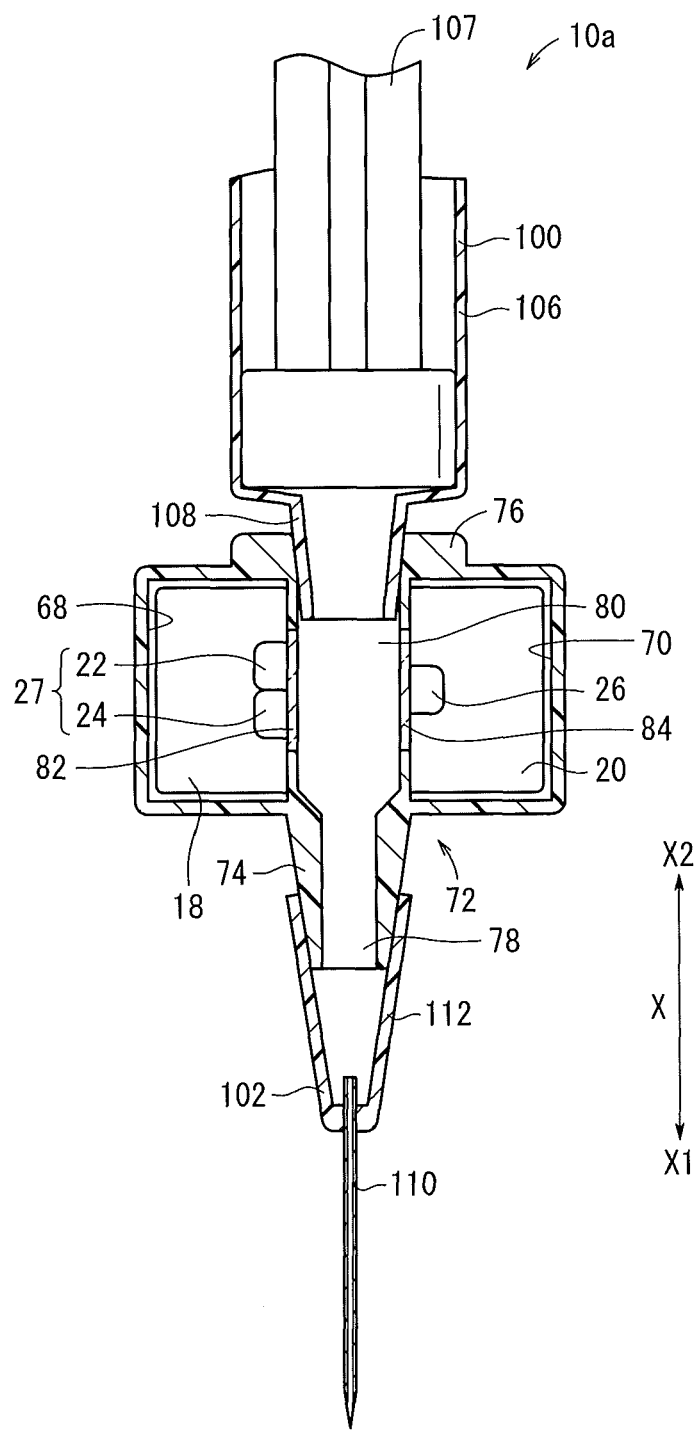
FIG. 6 is a sectional plan view of a partition in the first embodiment.

As shown in FIG. 6, the partition 72 has a distal-end joint portion 74 having a male Luer shape projecting in the X1-direction, a proximal-end joint portion 76 having a female Luer shape projecting in the X2-direction, and a blood inflow portion 78 permitting the distal-end joint portion 74 and the proximal-end joint portion 76 to communicate with each other along the X-direction.

Figure 7:
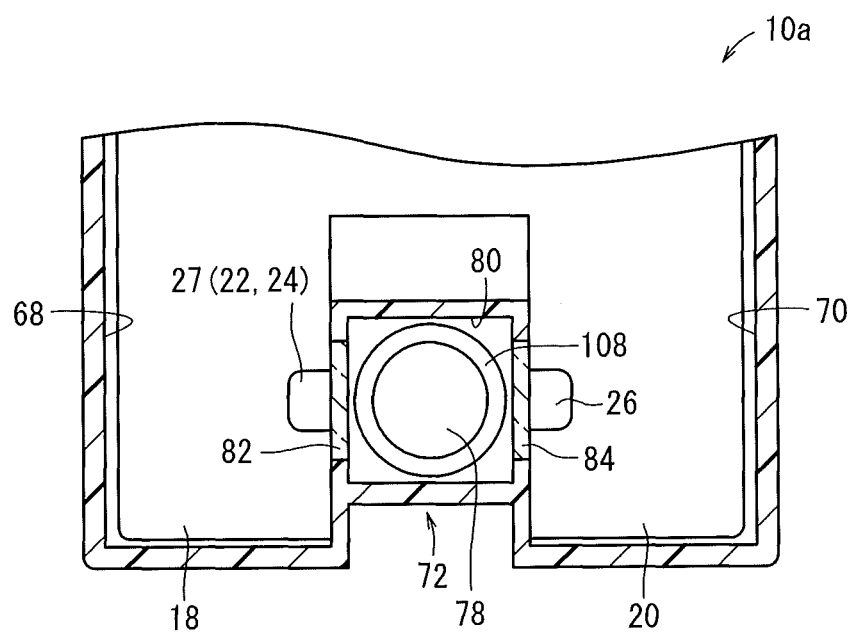
FIG. 7 is a sectional front view of the partition.

As shown in FIGS. 6 and 7, there is provided a measurement chamber 80 substantially quadrangular in front view at an intermediate portion of the blood inflow portion 78, and on left and right wall surfaces (attachment portions) of the measurement chamber 80, there are formed transparent measurement windows 82 and 84.

The measurement windows 82 and 84 are required only to ensure that light from the light projecting section 27 can be transmitted through the blood filling up the measurement chamber 80 and then measured by the light receiving element 26. Thus, the measurement windows 82 and 84 may not necessarily be transparent, and they may be colored or semi-transparent if they are thin to such an extent that light can be transmitted therethrough.

While the light projecting section 27 and the light receiving element 26 are disposed in the vicinity of the measurement windows 82 and 84, light from a light emitting body located in a remote place may be guided through a light guide body to the measurement windows 82 and 84. Incidentally, light guide bodies may be used for the blue output LED 28, the red output LED 30 and the green LED 32.

Where the main body 60 is colored, the measurement windows 82 and 84 may be formed appropriately thinly from the same material as that of the main body 60 or be formed from a transparent material different from the material of the main body 60. Where the main body 60 is transparent, other portions than the measurement windows 82 and 84 may be colored so that the other portions can block light. The coloring in this case may not necessarily be applied to the entire main body 60; for example, the swollen portion 66 may be colored at other portions than the measurement windows 82 and 84. For obtaining a high lightproof performance, the other portions than the measurement windows 82 and 84 may be colored black. Where light is blocked at least in the peripheries of the measurement windows 82 and 84, influences of disturbance light on the light projecting section 27 and the light receiving element 26 are lessened, and stable determination can be achieved.

The swollen portion 18 and the swollen portion 20 clamp the partition 72 therebetween, and no gap is present either between the light projecting section 27 and the measurement window 82 or between the light receiving element 26 and the measurement window 84. In addition, the measurement windows 82 and 84 are flat plates parallel to each other, are accompanied by little needless reflection or refraction of light, and are therefore suitable for optical measurement. Also, the swollen portion 18 and the swollen portion 20 clamp the partition 72 therebetween with an appropriate force, whereby the blood type determination unit 16a is stabilized.

Returning to FIG. 1, the main body 60 is provided at its inner side surface with a protrusion (switch operating section) 86 extending in the vertical direction. The protrusion 86 is located at such a position that the protrusion 86 fits into the groove 38 upon mounting of the blood type determination unit 16a to the main body 60, and is shaped such that the protrusion 86 pushes the power switch 40 at the position. The protrusion 86 has its top end inclined so as to permit easy fitting thereof into the groove 38.

The lid 64 is fixed through a process in which an engaging portion 88 of the lid 64 and an engaged portion 90 of the main body 60 are engaged with each other by folding of the hinge 62 (see FIG. 2). As a result, the main body 60 and the lid 64 are combined with each other to cover the blood type determination unit 16a, so that the blood type determination unit 16a will not be touched by a human hand. Thus, the blood type determination unit 16a can be covered simply by folding the lid 64, which ensures easy operation.

Of the periphery of the lid 64, three edges other than the edge where the hinge 62 is provided are provided with skirt portions 89 for covering the corresponding edges of an upper end of the main body 60.

On the lower side of the main body 60, there is provided a syringe holding member 91 having a circular arc cylindrical shape which is left and right symmetrical and is opened on the lower side. The syringe holding member 91 has an appropriate degree of elasticity, and can stably hold an outer cylinder 106 of the syringe 100 to be described later (see FIG. 2). The syringe holding member 91 may be transparent or provided with a visually checking window so that blood introduced into the syringe 100 can be easily visually confirmed.

As shown in FIG. 2, the lid 64 is provided with holes (output windows) 92, 94 and 96 for permitting visual checking of the blue output LED 28, the red output LED 30 and the green LED 32 provided at the upper surface of the blood type determination unit 16a. Annular protrusions 98 are provided respectively at the peripheries of the holes 92, 94 and 96 so that the blue output LED 28, the red output LED 30 and the green LED 32 are prevented from being touched by a human hand. The means for permitting visual checking of the blue output LED 28, the red output LED 30 and the green LED 32 is not limited to the holes, and may be any one that permits transmission of light therethrough, for example, transparent windows, thin portions, or the like.

Letters "VEIN" are presented in the vicinity of the hole 92, letters "ALTERY" in the vicinity of the hole 94, and letters "POWER" in the vicinity of the hole 96, which ensures easy understanding of the functions of the LEDs visible through the holes.

A syringe set (puncture tool) 14 is a general-purpose article, and has the syringe 100 and a needle body 102. The syringe 100 has a transparent outer cylinder 106, a plunger 107 with a gasket which is provided to be slidable inside the outer cylinder 106, and a male Luer-shaped reduced-diameter portion 108 at the distal end of the outer cylinder 106. The needle body 102 has a hollow needle 110 provided at the distal end thereof and a hub 112 for holding the needle 110. The hub 112 has a female Luer tapered shape, and is normally used in the state of being attached to the reduced-diameter portion 108 of the syringe 100. The syringe 100 and the needle body 102 are disposable articles which are preliminarily sterilized.

In the case of applying the set 10a for determining blood type to the syringe set 14, as shown in FIGS. 3 and 6, the reduced-diameter portion 108 of the syringe 100 is connected to the proximal-end joint portion 76, and the hub 112 is connected to the distal-end joint portion 74. As a result, the blood inflow portion 78 of the partition 72 is disposed between the syringe 100 and the needle body 102, and blood collected by the needle body 102 flows into the blood inflow portion 78.

Now, an individual package 120 for packaging the cover body 12a will be described below.

Figure 8:
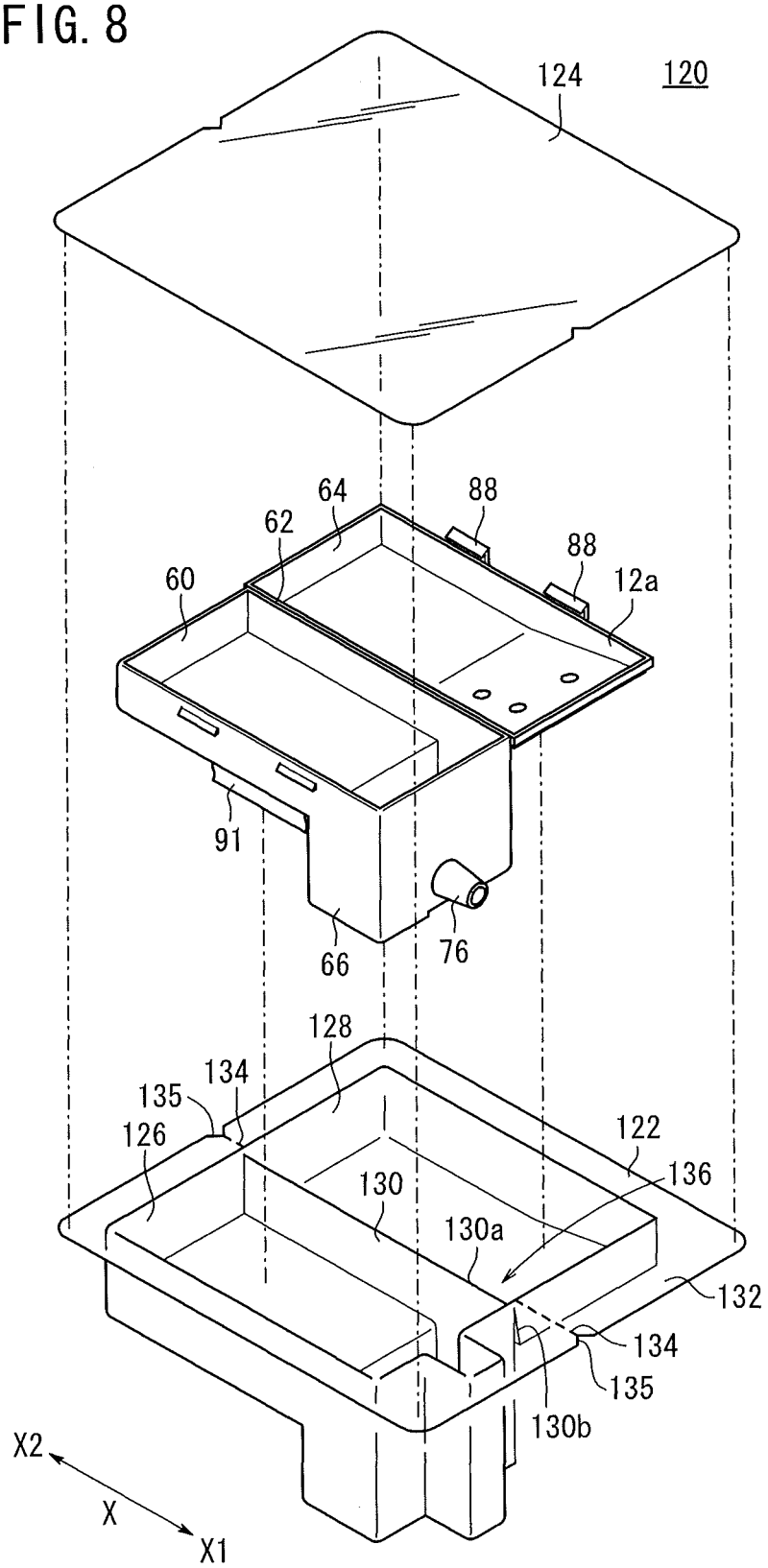
FIG. 8 is an exploded perspective view of an individual package in which a cover body is to be housed.
Figure 9:
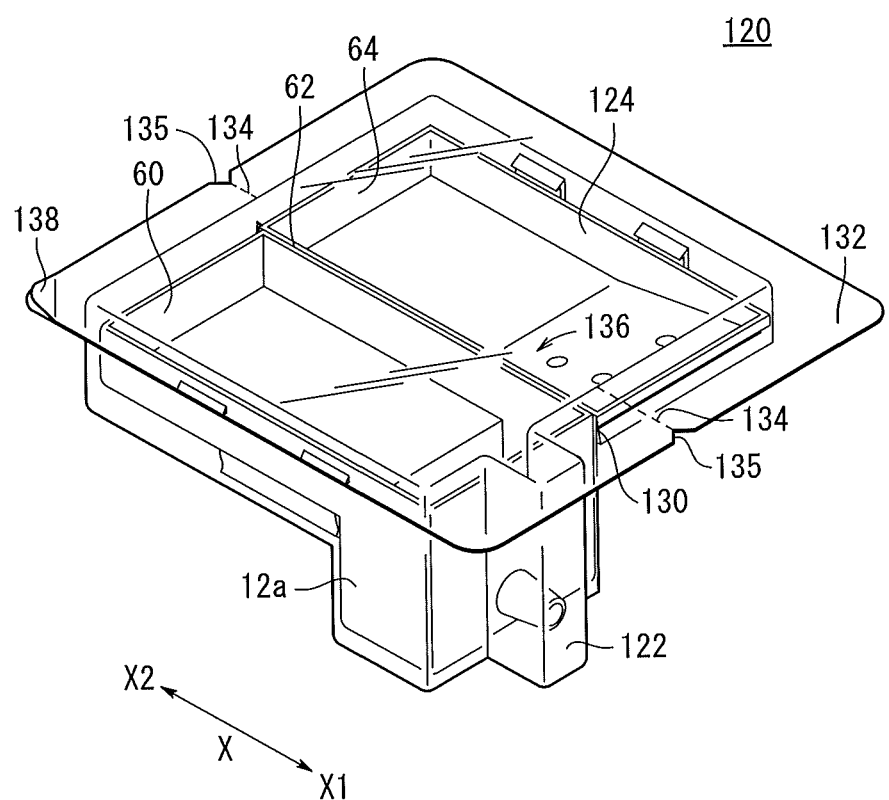
FIG. 9 is a perspective view of the individual package in which the cover body is to be housed.

As shown in FIGS. 8 and 9, the individual package 120 has a box body (tray) 122 for housing the cover body 12a therein with the main body 60 and the lid 64 being opened, and a film 124 for covering the upper surface of the box body 122. The box body 122 and the film 124 are in the same quadrangular shape in plan view. The film 124 covers an opening of the box body 122 so as to keep the inside of the individual package 120 in an aseptic condition, and can be detached from the box body 122 at the time of using the cover body 12a.

The box body 122 includes a first figure hole (first recess) 126 in which to mount the main body 60 of the cover body 12a, a second figure hole (second recess) 128 in which to mount the lid 64, a wall portion 130 of a boundary between the first figure hole 126 and the second figure hole 128, and a flange 132. The flange 132 is provided in the peripheries of the first figure hole 126 and the second figure hole 128, and the film 124 is attached to the flange 132. The first figure hole 126 and the second figure hole 128 are slightly deeper than the main body 60 and the lid 64 respectively, and are in the same shapes as the main body 60 and the lid 64 in plan view or in such shapes that the main body 60 and the lid 64 can be held therein, respectively.

The wall portion 130 has a first wall 130a constituting a surface of the first figure hole 126, and a second wall 130b constituting a surface of the second figure hole 128. The first wall 130a and the second wall 130b are connected to each other, at their edges on the side of opening upon removal of the film 124, to form a ridge line. The wall portion 130 constitutes an adjacency portion where parts of inner peripheral walls of the first figure hole 126 and the second figure hole 128 are adjacent to each other. The cover body 12a is housed in the box body 122 such that the hinge 62 is disposed at the adjacency portion. The wall portion 130 is disposed directly under the hinge 62, and its ridge line portion is positioned slightly below the flange 132. The flange 132 is provided with creases 134 on extension lines of both ends of the wall portion 130, for permitting folding thereat. The flange 132 is provided, at its portions on the outer sides of the two creases 134, with notches 135 for permitting easy folding along the creases 134. Either one of the crease 134 and the notch 135 may be provided. Instead of the notches 135, cut lines may be provided.

The ridge line portion at the top end of the wall portion 130 and the creases 134 are each set to be a substantially straight line in plan view and in side view. The crease 134 may be any structure that is relatively brittle so as to permit folding thereat, for example, perforation. The wall portion 130, the creases 134 and the notches 135, together with the hinge 62, constitute a folding portion 136 for folding the individual package 120 substantially at the center thereof. With the creases 134 and the notches 135 thus provided, they form a folding portion 136 together with the adjacency portion, whereby the adjacency portion of the box body 122 and the hinge 62 of the cover body 12 can be simultaneously bent in an appropriate manner.

The material of the box body 122 is formed into a thin plate as a whole. The material includes single-layer films of polyolefin resin such as polyethylene, polypropylene, etc., blended resin of these polyolefin resins, polyester resin such as polyethylene terephthalate, etc., polyvinylidene chloride, vinyl chloride-vinylidene chloride copolymer, etc., films obtained by vapor depositing aluminum, silica or the like on the above single-layer films, metallic foils such as aluminum film, aluminum laminate film, etc., and metallic foil-containing films. Further, laminate films obtained by laminating two or more of the above-mentioned films can be used. Also, a plastic non-woven fabric or paper may be used to form the box body 122.

The thickness of the box body 122 is not particularly limited and is appropriately determined depending on the layer configuration thereof, properties (flexibility, strength, water vapor permeability, heat resistance, etc.) of the material used, etc. Normally, the thickness of the box body 122 is preferably about 60 to 700 μm, more preferably about 100 to 500 μm.

The box body 122 can be produced by various methods such as inflation, T-die method, blow molding method, dry lamination, hot-melt lamination, co-extrusion inflation, co-extrusion T-die method, hot pressing method, etc.

The material of the film 124 includes polyesters such as polyethylene terephthalate (PET), etc., polyolefins such as polypropylene (PP), polystyrene (PS), polyethylene (PE), etc., polyvinyl chloride (PVC), polymethyl methacrylate (PMMA), polyether sulfone (PES), polypropylene-ethylene vinyl alcohol (EVOH) laminate, polypropylene-polyethylene laminate, nylon-polypropylene laminate, etc.

In the individual package 120, in order to secure visibility of the contents, it is preferable that at least one of the box body 122 and the film 124 is transparent.

The thickness of the film 124 is appropriately determined depending on the layer configuration thereof, properties (rigidity, strength, water vapor permeability, heat resistance, etc.) of the material used, etc. Normally, the thickness of the film 124 is preferably about 100 to 2000 μm, more preferably about 200 to 1000 μm.

The film 124 can be produced by various methods such as T-die method, dry lamination, hot-melt lamination, co-extrusion T-die method, hot pressing method, etc.

The box body 122 and the film 124 may be of the same configuration (material) or may be of different configurations (materials). For example, the flexibility of one of the box body 122 and the film 124 may be different from the flexibility of the other. Also, for instance, portions of the box body 122 other than the wall portion 130 and the creases 134 may be formed of a rigid material.

As shown in FIG. 9, a peripheral portion of the film 124 is sealed with respect to the flange 132 of the box body 122 by fusion (heat fusion, high-frequency fusion, ultrasonic fusion, etc.) or adhesion (adhesion with an adhesive or with a solvent), and the inside space of the thus sealed individual package 120 is isolated from the exterior. The individual package 120 is preliminarily subjected to electron-beam sterilization, γ-ray sterilization, EOG sterilization or the like, and its inside space inclusive of the cover body 12a is maintained in a sterile condition (inclusive of aseptic condition, here and hereinafter).

One corner portion of the film 124 is slightly peeled off from the flange 132, to constitute a peel tab 138 which can be gripped with fingers. At the time of using the individual package 120, the peel tab 138 is gripped and pulled, whereby the film 124 can be peeled from the box body 122, so that the cover body 12a inside the box body 122 is exposed.

Figure 10:
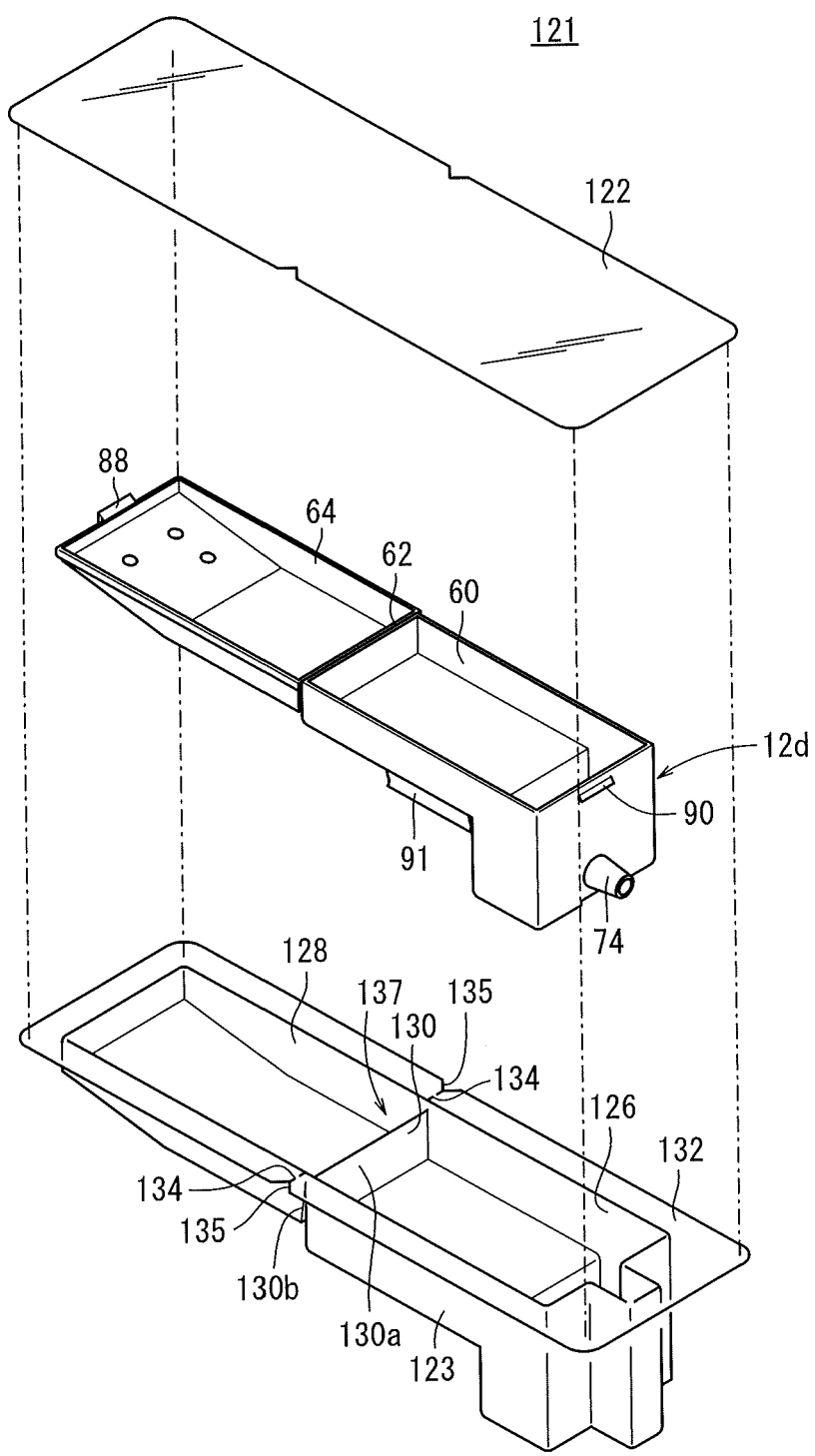
FIG. 10 is an exploded perspective view of an individual package according to a modification.

As a modification of the cover body 12a and the individual package 120, a cover body 12d and an individual package 121 of a longitudinally elongated form as shown in FIG. 10 can be used. The cover body 12d has a main body 60 and a lid 64 which are connected to each other by a hinge at a shorter edge portion thereof. A box body 122 of the individual package 121 has a longitudinally elongated shape adapted to the cover body 12d, and is provided, between a first figure hole 126 and a second figure hole 128, with a folding portion 137 for folding the individual package 121 and the cover body 12d substantially at the center thereof.

Now, in regard to the set 10a for determining blood type, the cover body 12a and the individual package 120, a method of using them and operations thereof during a surgical operation will be described below. Operation of these instruments is carried out separately by a first operator who touches only an affected part and sterilized medical instruments and by a second operator who operates other medical instruments. The first operator includes an operating surgeon, his/her assistant and the like, while the second operator includes a medical instrument technician, nurses and the like and also includes the first operator(s) before putting on sterilized gloves.

First, the second operator prepares the individual package 120, and pulls the peel tab 138 to peel off the film 124 from the box body 122, thereby exposing the cover body 12a inside the box body 122. At this time point, the cover body 12a is in a sterile condition.

Figure 11:
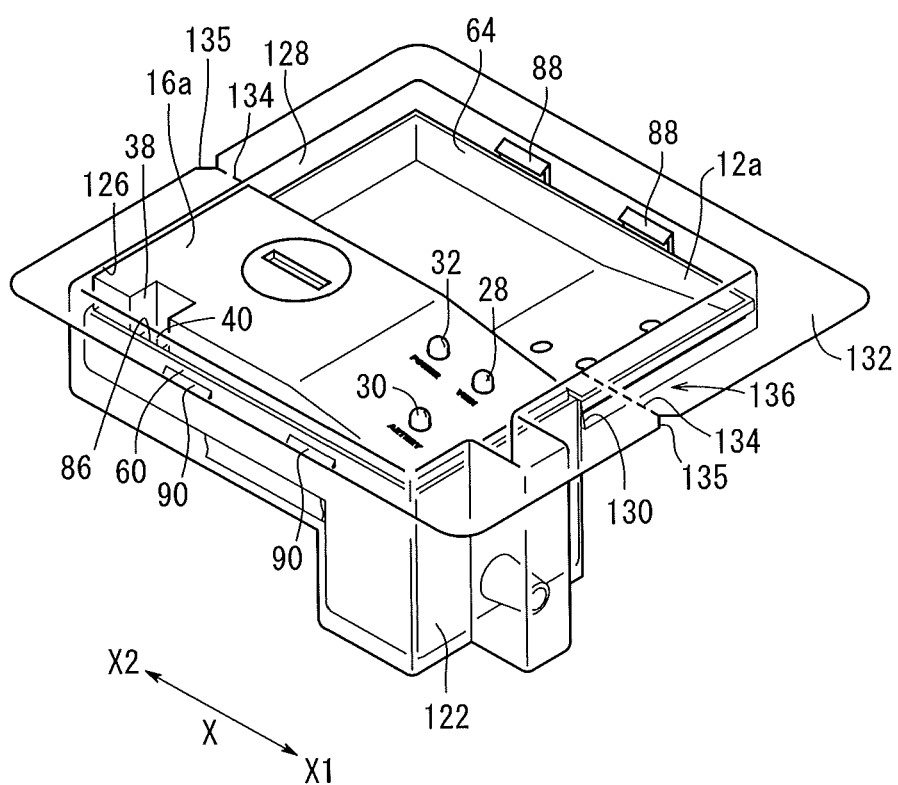
FIG. 11 is a perspective view showing a condition where a film of the individual package is peeled off and the blood type detection unit is mounted.

Next, as shown in FIG. 11, the second operator puts the blood type determination unit 16a in the main body 60 of the cover body 12a. Since the blood type determination unit 16a is not sterilized, the inner surface of the cover body 12a contacting with the blood type determination unit 16a is brought out of the sterile condition, but the outer surface of the cover body 12a is still maintained in the sterile condition. When the blood type determination unit 16a is mounted on the cover body 12a, the protrusion 86 pushes the power switch 40 to turn on the power supply, whereby the blood type determination unit 16a is started. The starting of the blood type determination unit 16a can be confirmed through turning-on of the green LED 32 serving as a power supply lamp.

Figure 12:
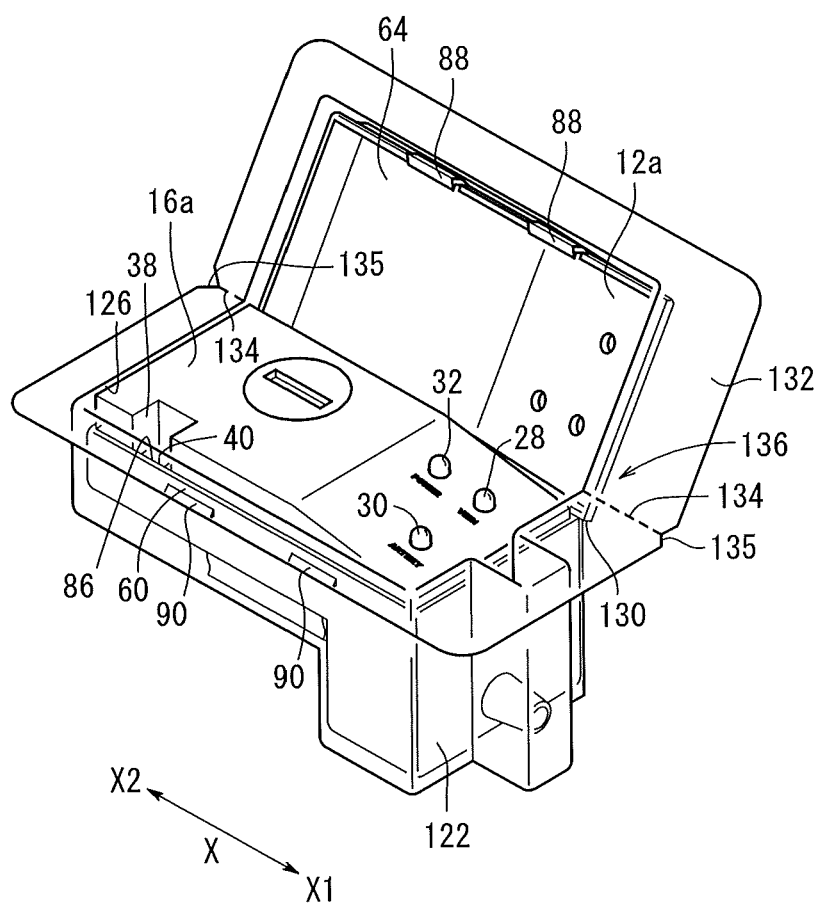
FIG. 12 is a perspective view showing a condition where a folding portion of a box body in the individual package is being folded.
Figure 13:
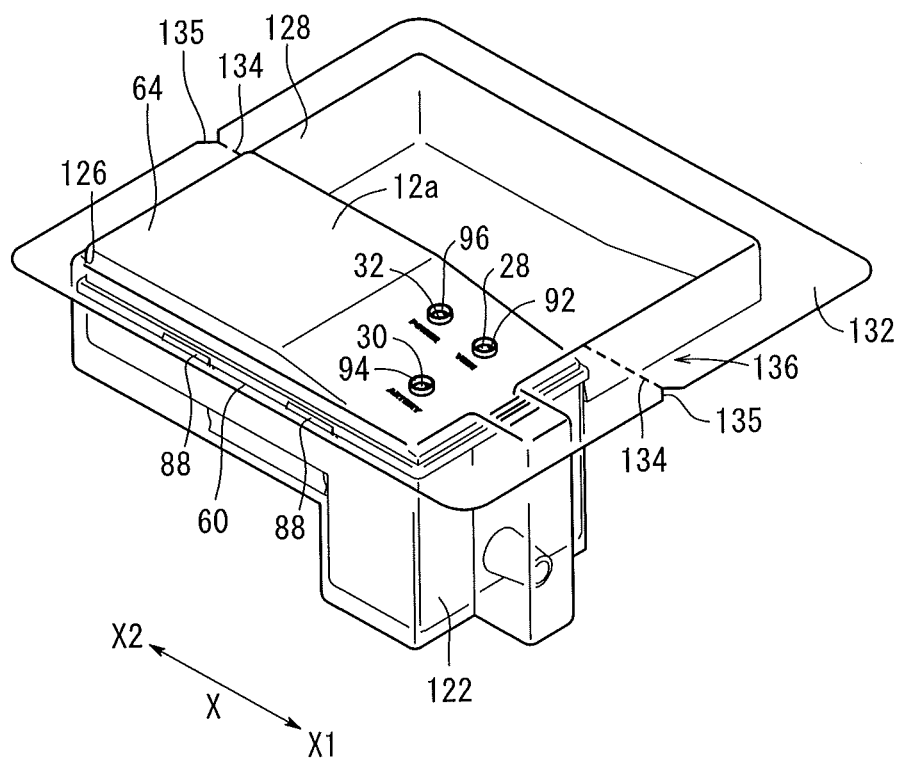
FIG. 13 is a perspective view showing a condition where the folding portion of the box body in the individual package is folded and a body and a lid of the cover body are engaged with each other.

As shown in FIGS. 12 and 13 in this order, the second operator folds the individual package 120 together with the cover body 12a at the folding portion 136 and the hinge 62. As a result, the engaging portion 88 and the engaged portion 90 are engaged with each other, and the cover body 12a is fixed in the state of housing the blood type determination unit 16a therein. At this time, the second operator is touching the individual package 120, and does not touch at least the outer surface of the cover body 12a, so that the outer surface of the cover body 12a is maintained in the sterile condition.

Subsequently, the first operator picks up the set 10a for determining blood type, having the cover body 12a and the blood type determination unit 16a combined with each other, out of the individual package 120. Then, the first operator mounts the sterilized syringe 100 and needle body 102 to the set 10a for determining blood type, as shown in FIG. 2.

Figure 14:
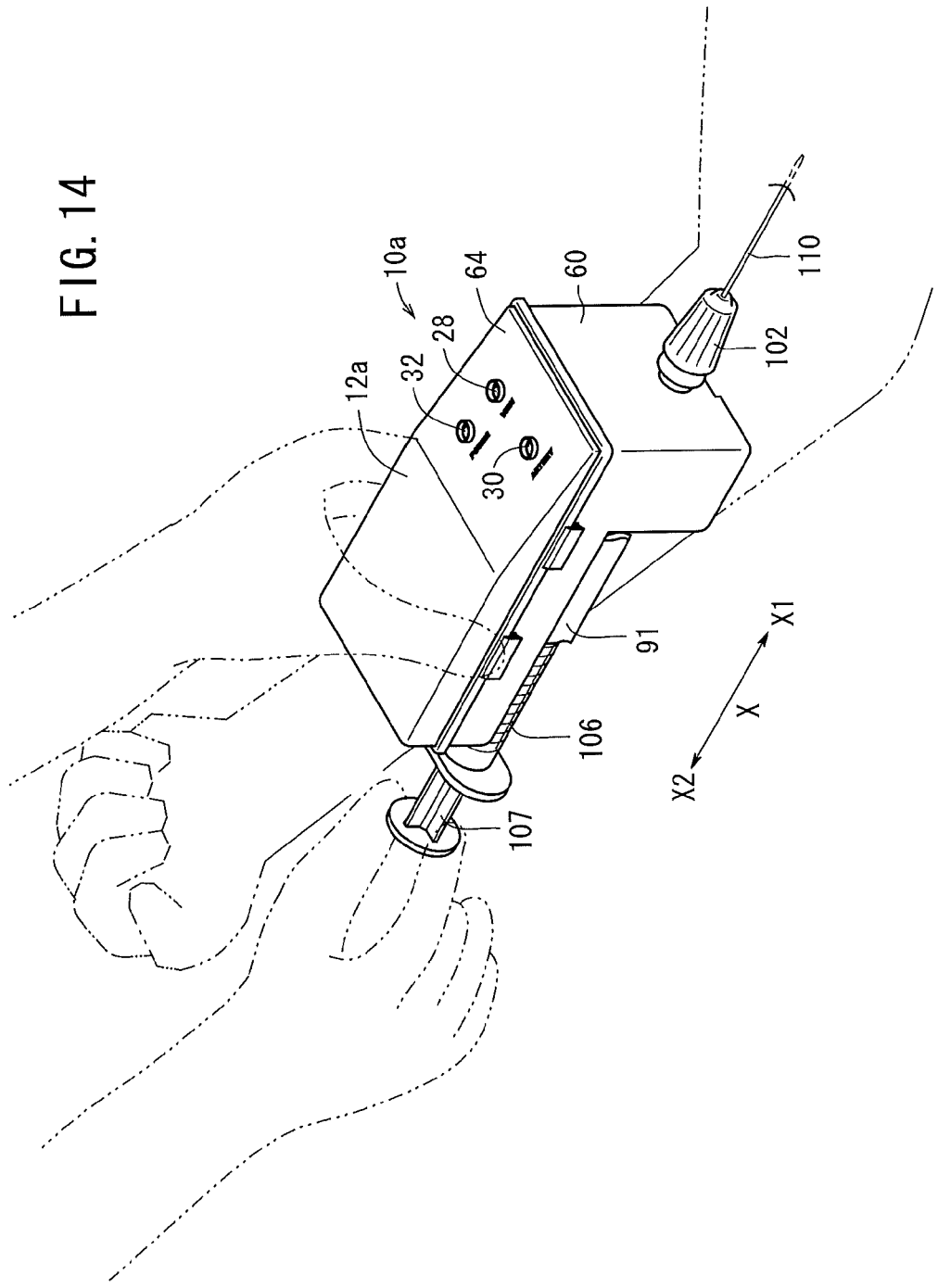
FIG. 14 is a perspective view of the set for determining blood type in use.

Further, as shown in FIG. 14, the first operator punctures a certain vein or artery of a patient with the needle 110 of the needle body 102 according to the purpose, and pulls the plunger 107. As a result of the puncturing and the operation of the plunger 107, blood is caused to flow through the needle 110 and the hub 112 into the blood inflow portion 78 (see FIG. 7), thereby filling up the blood inflow portion 78, and further to flow into the syringe 100. At this time, the blood type determination unit 16a inside the set 10a for determining blood type has already been started. Therefore, the lights emitted by the red measurement LED 22 and the infrared measurement LED 24 in predetermined patterns pass through the measurement window 82, the blood in the blood inflow portion 78 and the measurement window 84, to reach the light receiving element 26.

A signal received by the light receiving element 26 is supplied to the microcomputer 50, in which a signal processing is performed and it is determined whether the blood in the blood inflow portion 78 is venous blood or arterial blood. When the blood is venous blood, the blue output LED 28 is turned on; on the other hand, when the blood is arterial blood, the red output LED 30 is turned on. This permits the first operator to easily judge whether the blood obtained in the syringe 100 is venous blood or arterial blood. As is clear from FIG. 14, since the blue output LED 28, the red output LED 30 and the green LED 32 are provided on the X1-direction side of the upper surface of the cover body 12a, good visibility of the LEDs is ensured.

In the case where it is recognized based on the judgment result that an artery has erroneously been punctured when a vein is to be punctured or vice versa, a treatment such as blood stanching is carried out as required, and then the needle 110 is pulled off, and puncturing is carried out again.

After a predetermined procedure, the first operator pulls off the needle 110 from the patient. The first operator or the second operator detaches the syringe 100 and the needle body 102 from the set 10a for determining blood type. Further, the second operator opens the cover body 12a of the set 10a for determining blood type, and takes out the blood type determination unit 16a housed therein. The cover body 12a, the syringe 100 and the needle body 102 are disposable articles, and they are discarded according to a predetermined procedure.

In a series of operations as above described, the outer surface of the cover body 12a is maintained in a sterile condition, and the first operator touches only surfaces that are kept in a sterile condition.

According to the set 10a for determining blood type and the cover body 12a, the blood inflow portion 78 can be configured to be appropriately small in diameter and is accordingly filled up with blood speedily, so that the blood type can be judged early. In addition, since the wall surfaces of the partition (attachment portion) 72 and the blood inflow portion 78 are flat surfaces, the light projected from light projecting section 27 can be received by the light receiving element 26 without undergoing irregular reflection. The cover body 12a is applicable to general-purpose syringes 100 and needle bodies 102.

Now, a set 10b for determining blood type and a cover body 12b according to a second embodiment of the present invention will be described below. In the following, the same components as those of the set 10a for determining blood type and the cover body 12a will be denoted by the same reference numerals, and detailed descriptions thereof will be omitted.

Figure 15:
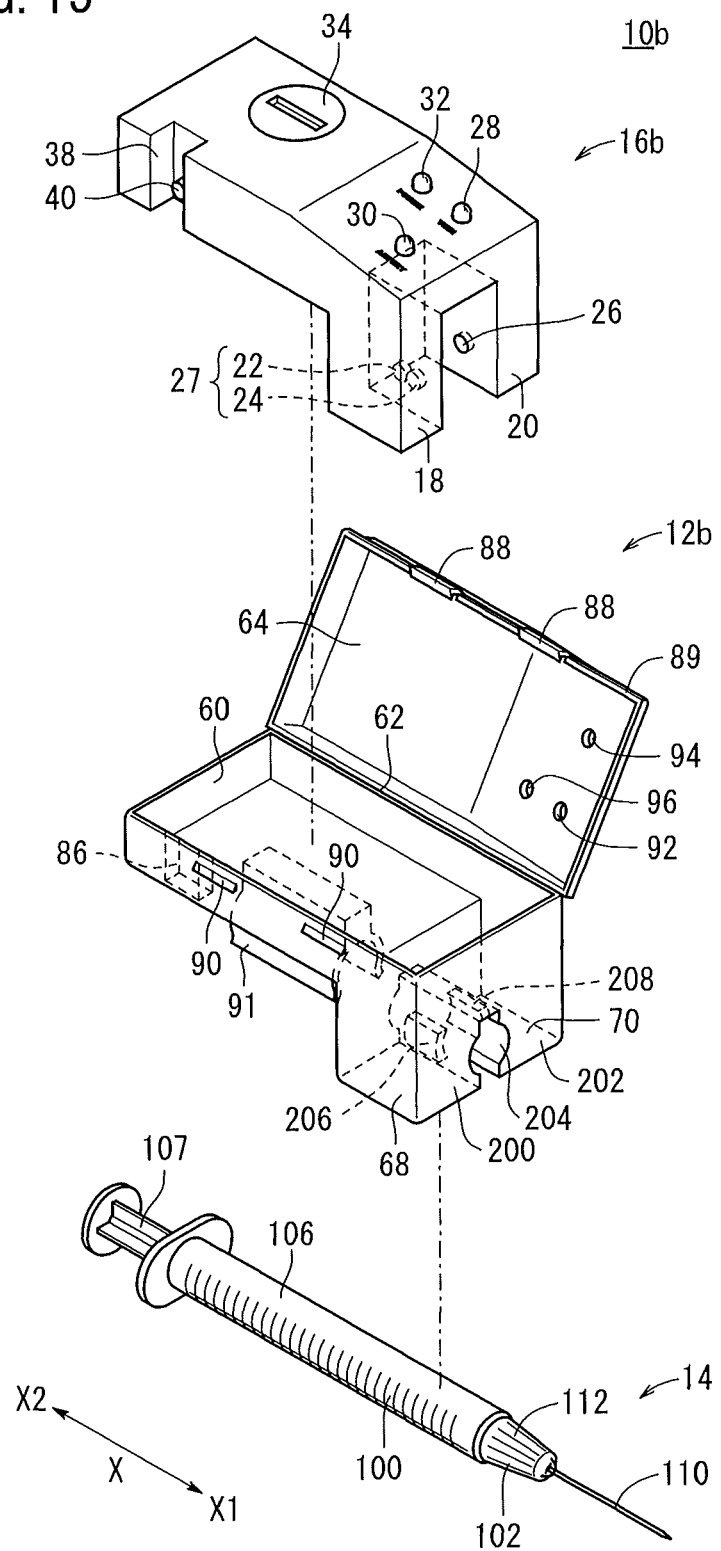
FIG. 15 is an exploded perspective view of a set for determining blood type according to a second embodiment of the present invention.
Figure 16:
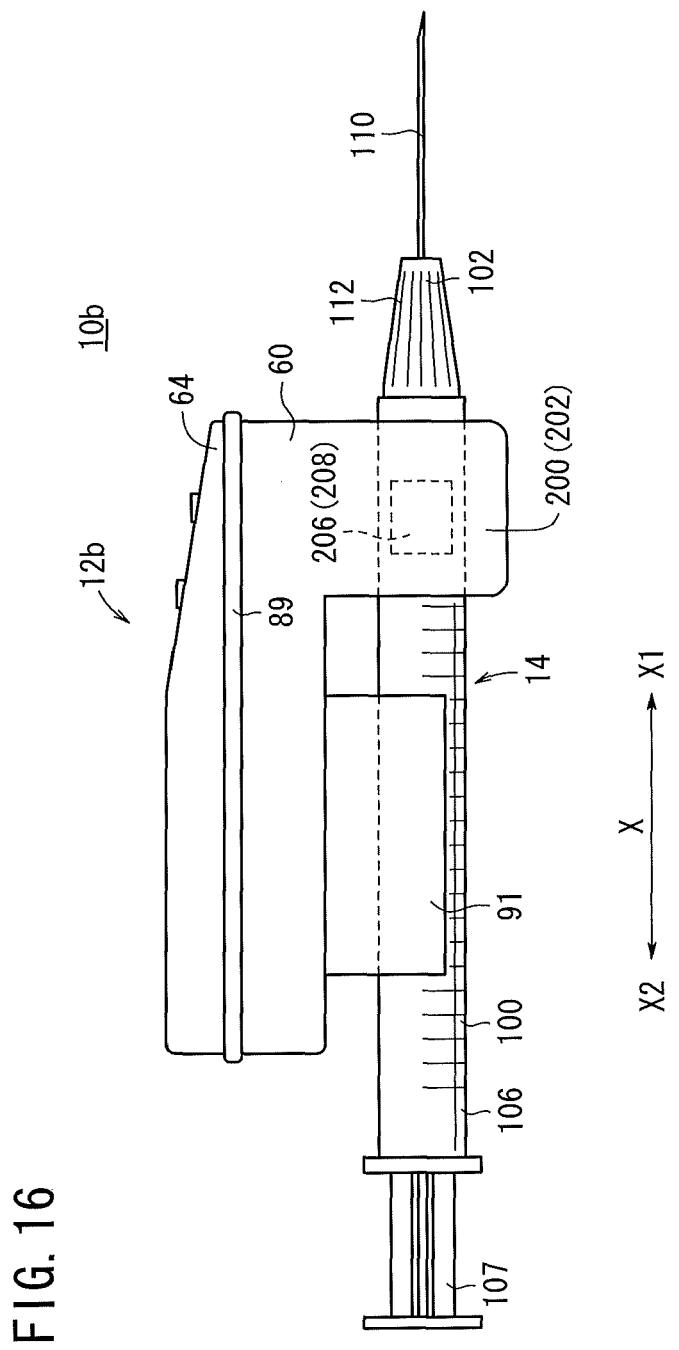
FIG. 16 is a side view of the set for determining blood type according to the second embodiment.

As shown in FIGS. 15 and 16, the set 10b for determining blood type, to be applied to a syringe set 14, has the cover body 12b to be attached to a syringe 100 of the syringe set 14, and a blood type determination unit 16b to be housed in the cover body 12b. The blood type determination unit 16b is configured in the same manner as the above-described blood type determination unit 16a, and has a shape corresponding to the cover body 12b. Though not shown in the drawings, the cover body 12b (and 12c) is packaged in a certain individual package and has been sterilized, in the same manner as the above-described cover body 12a.

The cover body 12b has swollen portions (measurement sections) 200 and 202 in which swollen portions 18 and 20 are to be inserted respectively. A gap portion (attachment portion) 204 between the swollen portion 200 and the swollen portion 202 has such a size that the gap portion 204 abuts against an outer cylinder 106 of the syringe 100.

Figure 17:
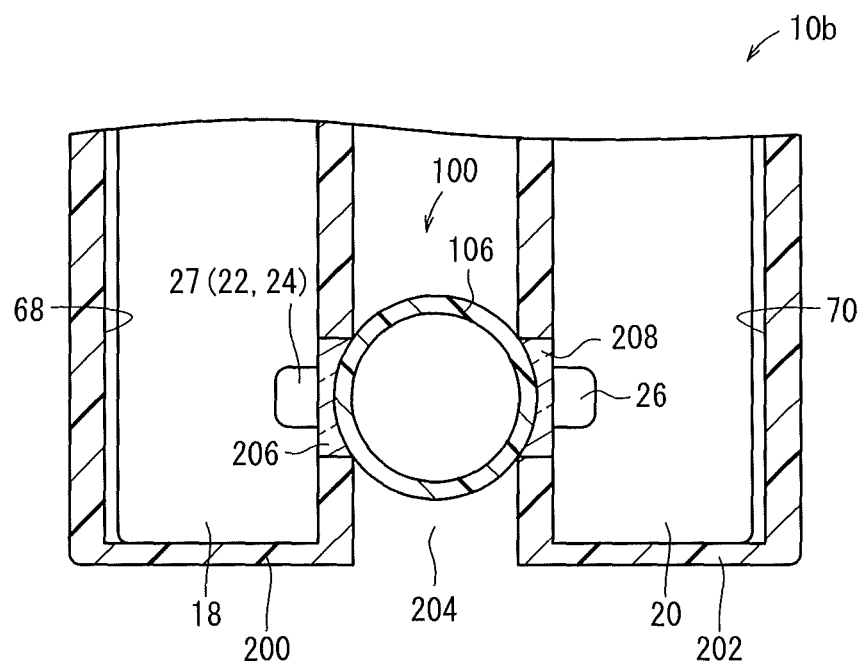
FIG. 17 is a sectional plan view of a partition in the second embodiment.

As shown in FIG. 17, a measurement window 206 of the swollen portion 200 and a measurement window 208 of the swollen portion 202 have surfaces facing each other. The surfaces are formed into a circular arc shape for abutment against a peripheral surface of the outer cylinder 106. Thus, the measurement windows 206, 208 abut against the outer cylinder 106 without any gap therebetween, whereby this system is stabilized optically and mechanically. The measurement windows 206 and 208 may be holes, insofar as the operators would not touch a light projecting section 27, a light receiving element 26 or their peripheries (namely, portions that are in a non-sterilized condition).

According to the set 10b for determining blood type and the cover body 12b configured as above-mentioned, the syringe set 14 can be used in an ordinary assembled condition (more specifically, in an assembled condition in which the needle body 102 is attached directly to the syringe 100), which ensures easy operation.

The outer cylinder 106 of the syringe 100 is normally transparent, so that in the set 10b for determining blood type and the cover body 12b, blood type can be judged through the outer cylinder 106.

Now, a set 10c for determining blood type and a cover body 12c according to a third embodiment of the present invention will be described below.

Figure 18:
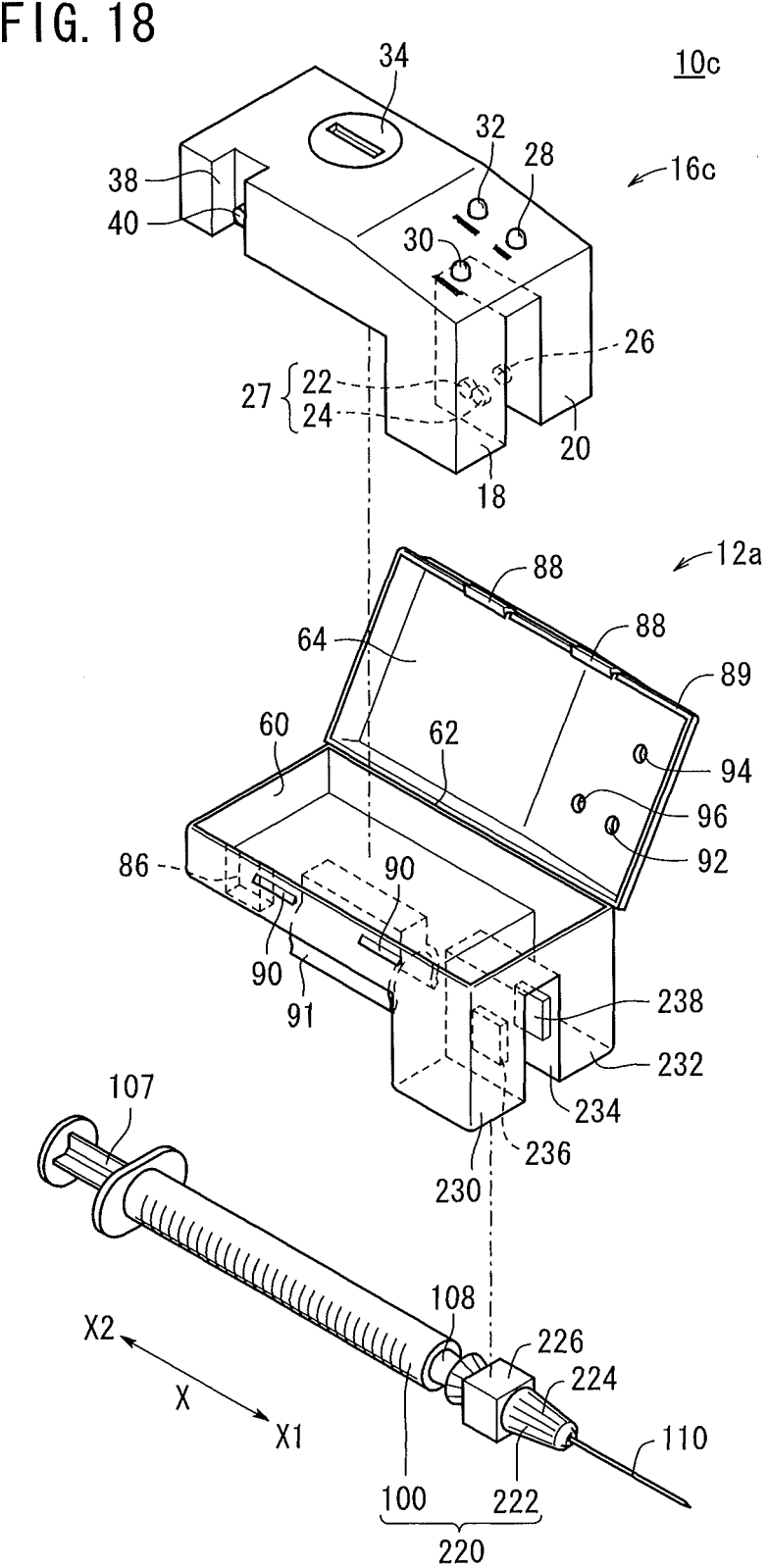
FIG. 18 is an exploded perspective view of a set for determining blood type according to a third embodiment of the present invention.
Figure 19:
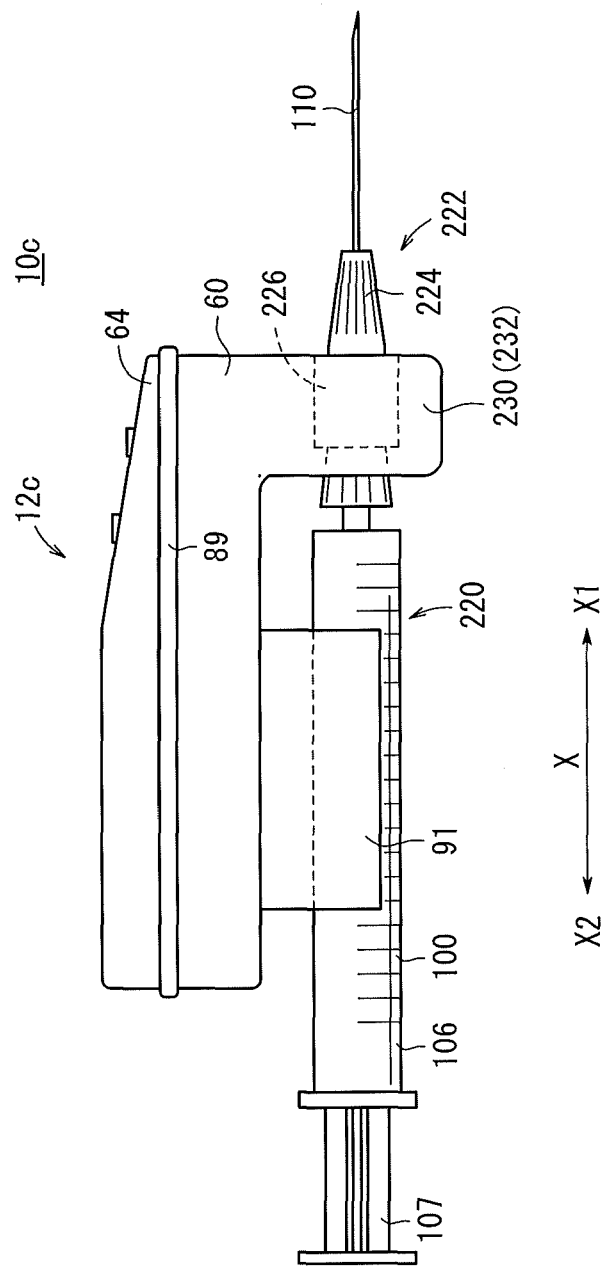
FIG. 19 is a side view of the set for determining blood type according to the third embodiment.

As shown in FIGS. 18 and 19, the set 10c for determining blood type is applied to a syringe set (puncture tool) 220. The syringe set 220 is composed of a needle body 222 and the above-mentioned syringe 100. The needle body 222 has a hollow needle 110 provided at the distal end thereof, and a hub 224 for holding the needle 110. The hub 224 has a female Luer tapered shape, and is used in the state of being attached to a reduced-diameter portion 108 of the syringe 100. The hub 224 is provided with a transparent body (blood inflow portion) 226 having a square cross section. The transparent body 226 has each side slightly greater than the outside diameter of the hub 224, and is small in size. The transparent body 226 is hollow, and forms a channel for blood. In the transparent body 226, other surfaces than left and right surfaces which face a measurement window 236 and a measurement window 238 may be lightproof. Incidentally, the hub 224 exclusive of the transparent body 226 is semi-transparent in color in order to indicate the size of the needle 110.

A blood type determination unit 16c is configured in the same manner as the above-described blood type determination unit 16a, and has a shape corresponding to the cover body 12c.

The cover body 12c has swollen portions (measurement sections) 230 and 232 in which swollen portions 18 and 20 are to be inserted respectively. A gap portion (attachment portion) 234 between the swollen portion 230 and the swollen portion 232 has such a size that the gap portion 234 abuts against the transparent body 226 of the hub 224.

Figure 20:
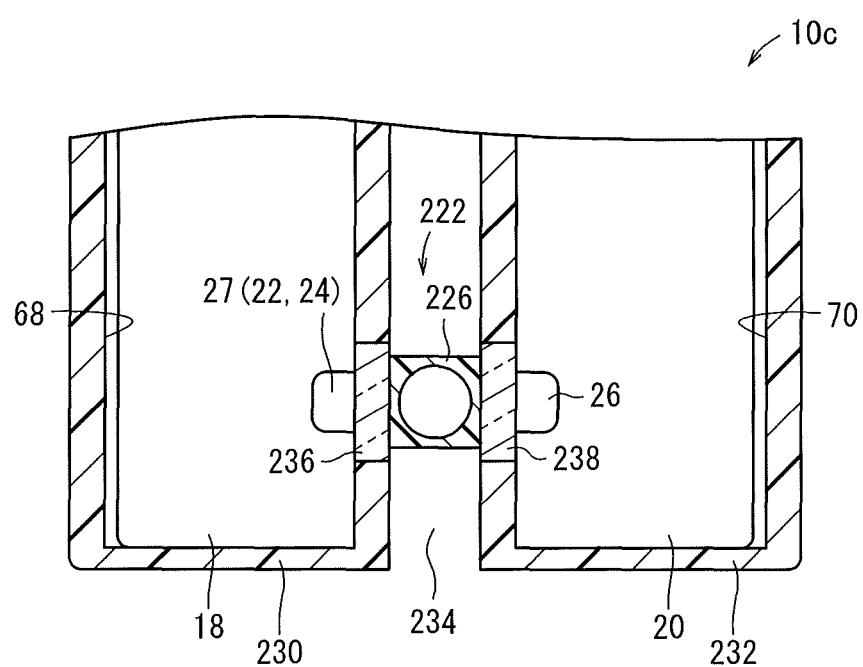
FIG. 20 is a sectional plan view of a partition in the third embodiment.

As shown in FIG. 20, the measurement window 236 of the swollen portion 230 and the measurement window 238 of the swollen portion 232 abut against the transparent body 226 without any gap therebetween, whereby this system is stabilized optically and mechanically.

The hub 224 and the transparent body 226 of the needle body 222 are small in size, so that they are filled up with blood speedily. Therefore, in the set 10c for determining blood type, the cover body 12c and the needle body 222, blood type as to blood passing through the transparent body 226 can be judged early.

The form of output is not limited to lamps such as the blue output LED 28 and the red output LED 30. For example, a liquid crystal display, a wireless output or a sound generator (sound or voice) may be used as the form of output in place of the lamps or may be used in combination with the lamps.

A sound generator generates different sounds between a case where the judgment result is venous blood and a case where the judgment result is arterial blood, whereby the judgment result can be recognized easily. Here, the term "different sounds" is used in a wide sense, and may be any distinguishable sounds, inclusive of those sounds which are different in tone color, sound volume, frequency, sound pattern, sound or the like. Further, in the cases of the wireless output or the output by the sound generator, the above-mentioned holes 92 and 94 (see FIG. 2) can be omitted. In regard to turning on/off of the power supply, a wireless output and an output by a sound generator can be used, and the above-mentioned green LED 32 and hole 96 can be omitted.

Figure 21:
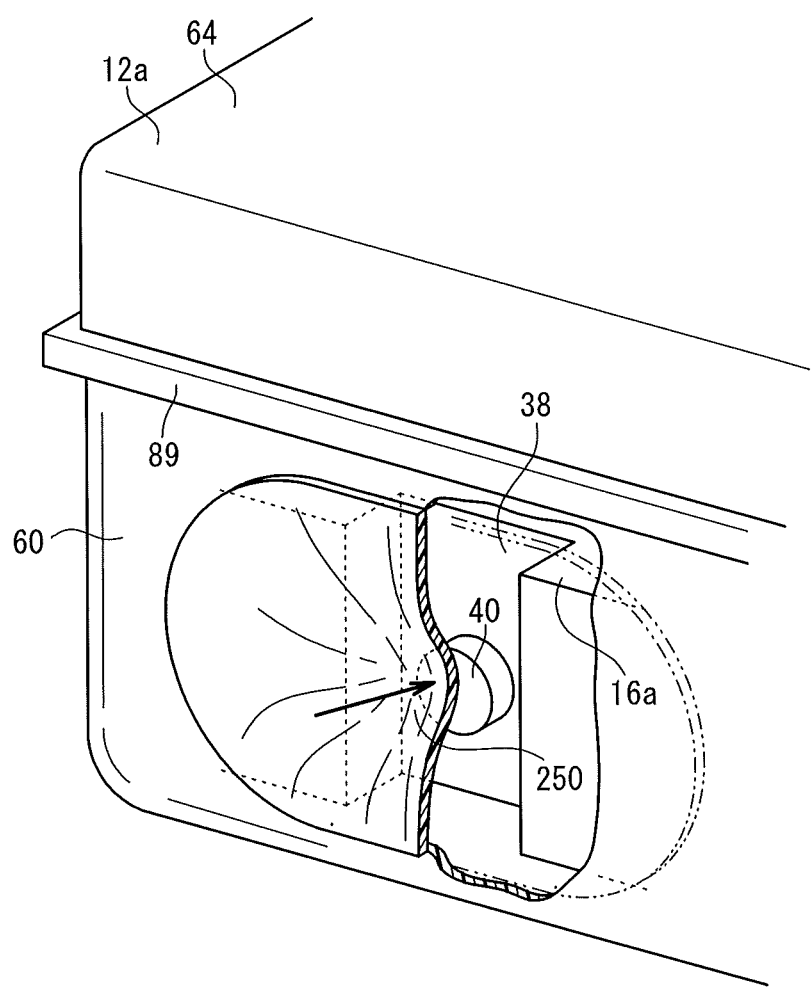
FIG. 21 is a perspective view, partly in section, of a periphery of a power switch according to a first modification.

While an example in which the power switch 40 is automatically operated by the protrusion 86 has been shown in the above-described embodiments, the cover body 12a may be provided with an elastic membrane (elastic portion) 250, and the elastic membrane 250 may be externally pushed and then elastically deformed to operate the power switch 40, as shown in FIG. 21. Owing thereto, while the blood type determination unit 16a is kept housed in the cover body 12, the power supply can be turned on/off at any timing without directly touching the blood type determination unit 16a.

Figure 22:
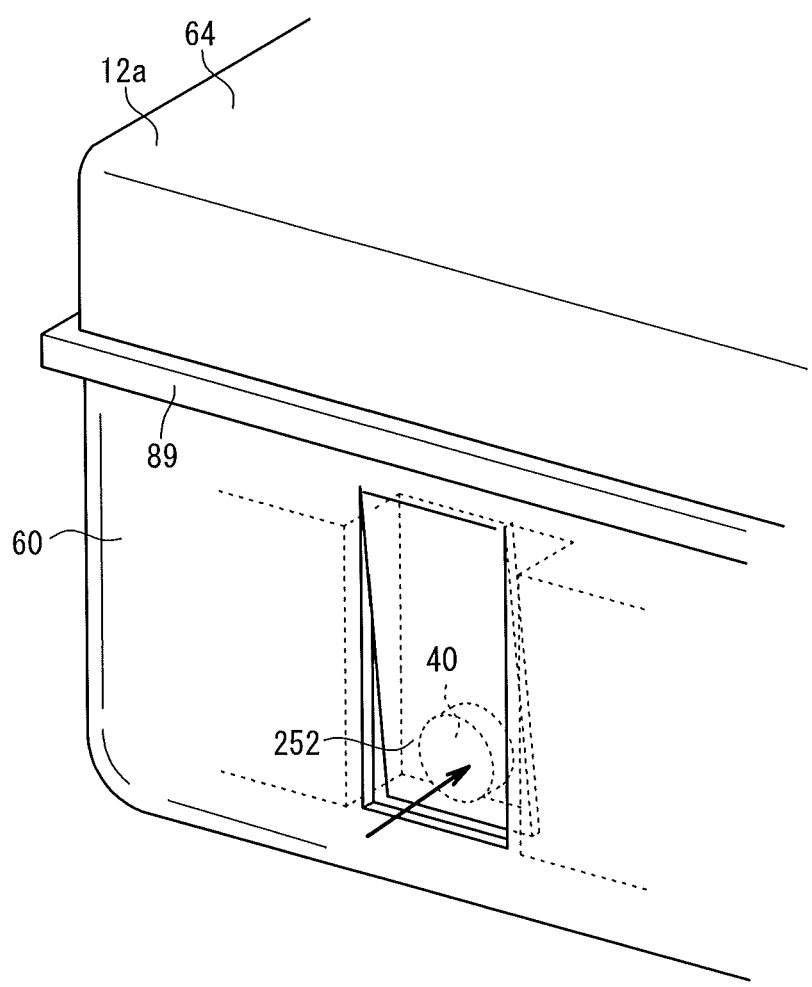
FIG. 22 is a perspective view of a periphery of a power switch according to a second modification.

The embodiments are not limited to the elastic membrane 250, and other configurations may also be adopted insofar as the blood type determination unit 16a inside would not be touched. For example, the power supply 40 may be operated through an elastic bent piece (elastic portion) 252 as shown in FIG. 22. In the cases where a configuration shown in FIGS. 21 and 22 is used, the groove 38 may be made shallower or wider so as to permit easier operation of the power switch 40, and the power switch 40 may be an alternate-type one.

As described above, in the sets 10a to 10c for determining blood type and the cover bodies 12a to 12d according to the embodiments of the present invention, the blood type determination unit 16a to 16c is covered with the cover body 12a to 12d so that the unit would not be touched by a human hand, and projection and reception of light with respect to the puncture tool are carried out through the predetermined measurement windows, whereby it can be easily judged whether the blood collected by the puncture tool is venous blood or arterial blood. The cover bodies 12a to 12d are simple in structure, and can be prepared as preliminarily sterilized disposable articles, so that the sets 10a to 10c for determining blood type can be operated in a sterile condition. As for the blood type determination units 16a to 16c, there is no need for disinfection or a special sterilizing treatment, and the units can be used as so-called reusable articles.

The cover body 12a to 12d is not limited to the configuration that is opened/closed through the hinge 62. Any configuration may be adopted insofar as the portions corresponding to the main body 60 and the lid 64 are combined with each other to cover the blood type determination unit 16a to 16c so that the unit would not be touched by a human hand. For example, the cover body 12a to 12d may be a slide type one or a shutter type one. The member for covering the blood type determination unit 16a to 16c is not limited to the two-member, i.e., the main body 60 and the lid 64. For example, the lid 64 may be divided into two portions to form a double hinged door type structure.

In addition, the puncture tool is not limited to a set of the needle body 102 and the syringe 100. For instance, a puncture tool for use in introducing a guide wire into a blood vessel (e.g., a puncture tool in which a needle body and a syringe are interconnected through a connector having a branched pipe equipped with a valve element, as described in Japanese Laid-Open Patent Publication No. 2007-000209) may be used. Further, a puncture tool in which a double needle (indwelling needle) composed of an inner needle and a catheter is used in place of the needle body may also be used.

The set for determining blood type and the cover body according to the present invention are not limited to those in the above-described embodiments, and, it should be understood that various configurations may be adopted without departing from the scope of the invention as set forth in the appended claims.

The invention claimed is:

1. A set for determining blood type, comprising:
a puncture tool;
a cover body defining an exterior and an interior; and
a blood type determination unit to be removably housed within an interior of the cover body, wherein the blood type determination unit includes
a light projecting section and a light receiving section which are located so as to face each other;

a judging section for determining whether blood between the light projecting section and the light receiving section is venous blood or arterial blood, based on a signal obtained from the light receiving section; and an output section for outputting the result of judgment made by the judging section;

wherein the exterior of the cover body comprises a joint portion configured for attachment of the puncture tool thereto such that blood collected by the puncture tool flows into a space between the light projecting section and the light receiving section.

2. The set for determining blood type according to claim 1, wherein the cover body has a first cover member and a second cover member connected to the first cover member by a hinge, the first cover member including a measurement section, and the blood type determination unit being mounted in the first cover member.

3. The set for determining blood type according to claim 2, wherein the measurement section has an attachment portion to be attached to the puncture tool, and a measurement window provided on the attachment portion and through which light is transmitted between the light projecting section and the light receiving section.

4. The set for determining blood type according to claim 3, wherein at least a periphery of the measurement window of the measurement section is lightproof.

5. The set for determining blood type according to claim 3, wherein the puncture tool has a needle body and a syringe;

the attachment portion has a blood inflow portion which is disposed between the needle body and the syringe and into which blood is introduced; and the needle body and the syringe are connected to the blood inflow portion.

6. The set for determining blood type according to claim 3, wherein the puncture tool has a needle body and a syringe; and the attachment portion is attached to an outer cylinder of the syringe.

7. The set for determining blood type according to claim 3, wherein the puncture tool has a needle body and a syringe; and the attachment portion is attached to a blood inflow portion which is formed at a hub of the needle body and into which blood is introduced.

8. The set for determining blood type according to claim 1, wherein the output section has a first lamp for emitting light when the result of judgment by the judging section is venous blood, and a second lamp for emitting light when the result of judgment by the judging section is arterial blood.

9. The set for determining blood type according to claim 1, wherein the blood type determination unit has a power switch; and the cover body has a switch operating section which, when the blood type determination unit is placed therein, abuts against the power switch to turn on a power supply for the blood type determination unit.

10. The set for determining blood type according to claim 1, wherein the puncture tool has a needle body and a syringe, and the cover body has a syringe holding member for holding the syringe.

11. An assembly comprising:

a cover body which removably houses therein a blood type determination unit and which is attached to a puncture tool, the blood type determination unit including:

a light projecting section and a light receiving section that are located so as to face each other;

a judging section for determining whether blood between the light projecting section and the light receiving section is venous blood or arterial blood, based on a signal obtained from the light receiving section; and an output section for outputting the result of judgment by the judging section, wherein the cover body comprises a measurement section, an exterior of which includes a joint portion configured to be attached to the puncture tool such that blood collected by the puncture tool flows into a space between the light projecting section and the light receiving section.

* * * * *